(12) United States Patent
Fisher et al.

(10) Patent No.: US 8,828,013 B2
(45) Date of Patent: Sep. 9, 2014

(54) BONE POSITIONING DEVICE AND METHOD

(75) Inventors: Michael G. Fisher, Reno, NV (US);
Anthony K. Hedley, Paradise Valley, AZ (US); Russell T. Nevins, Las Vegas, NV (US); Kenneth D. Johannaber, Rancho Murieta, CA (US); Kevin M. Cordes, Rancho Cordova, CA (US)

(73) Assignee: Synvasive Technology, Inc., El Dorado Hills, CA (US)

( * ) Notice: Subject to any disclaimer, the term of this patent is extended or adjusted under 35 U.S.C. 154(b) by 556 days.

(21) Appl. No.: 12/729,222

(22) Filed: Mar. 22, 2010

(65) Prior Publication Data

US 2011/0106092 A1 May 5, 2011

Related U.S. Application Data

(63) Continuation-in-part of application No. 12/616,747, filed on Nov. 11, 2009, now Pat. No. 8,435,246, and a continuation of application No. PCT/US2009/063015, filed on Nov. 2, 2009.

(51) Int. Cl.
*A61B 17/15* (2006.01)
*A61B 19/00* (2006.01)

(52) U.S. Cl.
CPC .......... *A61B 17/157* (2013.01); *A61B 2019/462* (2013.01); *A61B 19/201* (2013.01); *A61B 2019/202* (2013.01); *A61B 2019/4836* (2013.01)
USPC .......................................................... 606/88

(58) Field of Classification Search
USPC ......... 606/86 R–88; 623/18.11, 20.14, 20.21, 623/20.32, 23.39
See application file for complete search history.

(56) References Cited

U.S. PATENT DOCUMENTS

| | | | |
|---|---|---|---|
| 1,179,910 | A | 4/1916 | Greenfield |
| 1,201,467 | A | 10/1916 | Hoglund |
| 1,726,241 | A | 8/1929 | Schubert |
| 2,702,550 | A | 2/1955 | Rowe |
| 2,854,981 | A | 10/1958 | Marshal |
| 3,554,197 | A | 1/1971 | Dobbie |
| 3,678,934 | A | 7/1972 | Warfield et al. |
| 3,978,862 | A | 9/1976 | Morrison |

(Continued)

FOREIGN PATENT DOCUMENTS

| | | |
|---|---|---|
| CA | 2870063 A1 | 5/2011 |
| EP | 1444957 A1 | 8/2004 |

(Continued)

OTHER PUBLICATIONS

PCT International Search Report and Written Opinion mailed on Jan. 10, 2011 issued in PCT Application No. PCT/US2010/028729.

(Continued)

*Primary Examiner* — Matthew Lawson
*Assistant Examiner* — Zade Coley
(74) *Attorney, Agent, or Firm* — Schwegman Lundberg & Woessner, P.A.

(57) ABSTRACT

A method for positioning a bone cut on a bone may involve: coupling a bone cut positioning apparatus with a body bone; adjusting the positioning apparatus in a varus/valgus orientation relative to the body bone; adjusting the positioning apparatus in an anterior/posterior orientation relative to the body bone; and adjusting the positioning apparatus up or down to select a bone resection level.

13 Claims, 41 Drawing Sheets

(56) References Cited

U.S. PATENT DOCUMENTS

| | | | |
|---|---|---|---|
| 4,153,742 A | 5/1979 | Boehn et al. | |
| 4,567,798 A | 2/1986 | Brdicko | |
| 4,567,886 A | 2/1986 | Petersen | |
| 4,584,999 A | 4/1986 | Arnegger | |
| 4,617,930 A | 10/1986 | Saunders | |
| 4,768,504 A | 9/1988 | Ender | |
| 4,872,095 A * | 10/1989 | Dubak et al. | 362/100 |
| 4,952,213 A | 8/1990 | Bowman et al. | |
| 5,087,261 A | 2/1992 | Ryd et al. | |
| 5,092,869 A | 3/1992 | Waldron et al. | |
| 5,116,344 A * | 5/1992 | Sundqvist | 606/130 |
| 5,122,142 A | 6/1992 | Pascaloff et al. | |
| 5,147,365 A | 9/1992 | Whitlock et al. | |
| 5,178,626 A | 1/1993 | Pappas et al. | |
| 5,201,749 A | 4/1993 | Sachse et al. | |
| 5,263,972 A | 11/1993 | Evans et al. | |
| 5,306,285 A | 4/1994 | Miller et al. | |
| 5,382,249 A | 1/1995 | Fletcher et al. | |
| 5,403,318 A | 4/1995 | Boehringer et al. | |
| 5,409,491 A | 4/1995 | Boehringer et al. | |
| 5,437,676 A | 8/1995 | Bouraly et al. | |
| 5,439,472 A | 8/1995 | Evans et al. | |
| 5,496,325 A | 3/1996 | McIees | |
| 5,507,763 A | 4/1996 | Petersen et al. | |
| 5,554,165 A | 9/1996 | Raitt et al. | |
| 5,569,257 A | 10/1996 | Arnegger et al. | |
| 5,624,444 A | 4/1997 | Wixon et al. | |
| 5,681,316 A | 10/1997 | DeOrio et al. | |
| 5,735,866 A | 4/1998 | Adams et al. | |
| 5,839,196 A | 11/1998 | Trott | |
| 5,846,244 A | 12/1998 | Cripe | |
| 5,916,220 A | 6/1999 | Masini | |
| 6,022,353 A | 2/2000 | Fletcher et al. | |
| 6,063,091 A | 5/2000 | Lombardo et al. | |
| 6,090,114 A | 7/2000 | Matsuno et al. | |
| 6,503,253 B1 | 1/2003 | Fletcher et al. | |
| 6,514,259 B2 | 2/2003 | Picard et al. | |
| 6,595,997 B2 | 7/2003 | Axelson, Jr. et al. | |
| 6,656,186 B2 | 12/2003 | Meckel | |
| 6,723,101 B2 | 4/2004 | Fletcher et al. | |
| 6,846,230 B2 | 1/2005 | Jonas | |
| 6,875,222 B2 | 4/2005 | Long et al. | |
| 6,896,679 B2 | 5/2005 | Danger et al. | |
| 7,104,996 B2 | 9/2006 | Bonutti | |
| 7,442,196 B2 | 10/2008 | Fisher et al. | |
| 7,497,860 B2 | 3/2009 | Carusillo et al. | |
| 7,527,628 B2 | 5/2009 | Fletcher et al. | |
| 7,578,821 B2 | 8/2009 | Fisher et al. | |
| 7,704,254 B2 | 4/2010 | Walen et al. | |
| 7,857,821 B2 | 12/2010 | Couture et al. | |
| 8,435,246 B2 | 5/2013 | Fisher et al. | |
| 2002/0116022 A1 | 8/2002 | Lebouitz et al. | |
| 2002/0133161 A1 | 9/2002 | Axelson, Jr. et al. | |
| 2002/0198556 A1 | 12/2002 | Ark et al. | |
| 2003/0014067 A1 | 1/2003 | Kullmer et al. | |
| 2003/0075162 A1 | 4/2003 | Hamilton | |
| 2003/0153978 A1* | 8/2003 | Whiteside | 623/20.21 |
| 2004/0039396 A1* | 2/2004 | Couture et al. | 606/87 |
| 2004/0172044 A1 | 9/2004 | Grimm et al. | |
| 2004/0199167 A1 | 10/2004 | Fletcher et al. | |
| 2004/0243136 A1 | 12/2004 | Gupta et al. | |
| 2005/0021039 A1 | 1/2005 | Cusick et al. | |
| 2005/0065530 A1 | 3/2005 | Stauch et al. | |
| 2005/0070897 A1 | 3/2005 | Petersen | |
| 2005/0113846 A1* | 5/2005 | Carson | 606/130 |
| 2005/0143746 A1* | 6/2005 | Steffensmeier et al. | 606/88 |
| 2005/0222573 A1* | 10/2005 | Branch et al. | 606/86 |
| 2005/0240196 A1 | 10/2005 | Davis et al. | |
| 2005/0267485 A1 | 12/2005 | Cordes et al. | |
| 2006/0241639 A1 | 10/2006 | Kuczynski et al. | |
| 2007/0043375 A1* | 2/2007 | Anissian | 606/87 |
| 2007/0083209 A1 | 4/2007 | Schenberger et al. | |
| 2007/0119055 A1 | 5/2007 | Walen et al. | |
| 2007/0123893 A1 | 5/2007 | O'Donoghue | |
| 2007/0219559 A1* | 9/2007 | Heavener et al. | 606/87 |
| 2008/0027449 A1 | 1/2008 | Gundlapalli et al. | |
| 2008/0065085 A1 | 3/2008 | Couture et al. | |
| 2008/0195109 A1 | 8/2008 | Hunter et al. | |
| 2008/0243125 A1 | 10/2008 | Guzman et al. | |
| 2009/0043310 A1 | 2/2009 | Rasmussen | |
| 2009/0093814 A1 | 4/2009 | Fletcher et al. | |
| 2009/0093815 A1 | 4/2009 | Fletcher et al. | |
| 2009/0234360 A1* | 9/2009 | Alexander | 606/88 |
| 2011/0106092 A1 | 5/2011 | Fisher et al. | |
| 2012/0245589 A1 | 9/2012 | Fisher et al. | |

FOREIGN PATENT DOCUMENTS

| | | | | |
|---|---|---|---|---|
| WO | WO-2007030793 A2 | | 3/2007 | |
| WO | WO-2008/073999 | * | 6/2008 | A61N 5/067 |
| WO | WO 2008073999 A2 | * | 6/2008 | A61B 17/15 |
| WO | WO-2013134595 A1 | | 9/2013 | |

OTHER PUBLICATIONS

PCT International Search Report and Written Opinion mailed on Jul. 27, 2010.

"U.S. Appl. No. 12/616,747, Notice of Allowance mailed Jan. 10, 2013", 7 pgs.

"European Application Serial No. 10827286.5, Office Action mailed Jun. 14, 2012", 2 pgs.

"European Application Serial No. 10827286.5, Response filed Dec. 19, 2012 to Office Action mailed Jun. 14, 2012", 9 pgs.

"U.S. Appl. No. 12/616,747, Examiner Interview Summary mailed Jul. 31, 2012", 3 pgs.

"U.S. Appl. No. 12/616,747, Final Office Action mailed Apr. 20, 2012", 11 pgs.

"U.S. Appl. No. 12/616,747, Non Final Office Action mailed Mar. 15, 2012", 12 pgs.

"U.S. Appl. No. 12/616,747, Notice of Allowance mailed Sep. 28, 2012", 10 pgs.

"U.S. Appl. No. 12/616,747, Preliminary Amendment filed Nov. 11, 2009", 10 pgs.

"U.S. Appl. No. 12/616,747, Response filed Mar. 30, 2012 to Non Final Office Action mailed Mar. 15, 2012", 12 pgs.

"U.S. Appl. No. 12/616,747, Response filed Aug. 15, 2012 to Final Office Action mailed Apr. 20, 2012", 10 pgs.

"International Application Serial No. PCT/US2009/063015, International Preliminary Report on Patentability mailed May 8, 2012", 6 pgs.

"International Application Serial No. PCT/US2009/063015, International Search Report mailed Jul. 27, 2010", 4 pgs.

"International Application Serial No. PCT/US2009/063015, Written Opinion mailed Jul. 27, 2010", 5 pgs.

"U.S. Appl. No. 13/417,079, Non Final Office Action mailed Nov. 15, 2013", 12 pgs.

"U.S. Appl. No. 13/417,079, Response filed Mar. 14, 2014 to Non-Final Office action mailed Nov. 15, 2013", 13 pgs.

"U.S. Appl. No. 13/417,079, Response filed Mar. 14, 2014 to Restriction Requirement mailed Sep. 25, 2013 and Non-Final Office Action mailed Nov. 15, 2013", 11 pgs.

"U.S. Appl. No. 13/417,079, Response filed Oct. 25, 2013 to Restriction Requirement mailed Sep. 25, 2013", 9 pgs.

"U.S. Appl. No. 13/417,079, Restriction Requirement mailed Sep. 25, 2013", 6 pgs.

"International Application Serial No. PCT/US2013/029767, International Search Report mailed Jun. 14, 2013", 6 pgs.

"International Application Serial No. PCT/US2013/029767, Written Opinion mailed Jun. 14, 2013", 7 pgs.

Stryker, "Precision Oscillating Tip Saw—Ref 6209, Instruction for Use", 6209-001-708 Rev-A, (2006), 21 pgs.

Stryker, "Precision Oscillating Tip Saw [pamphlet]", Literature No. MTX9100001044, (2006), 2 pgs.

* cited by examiner

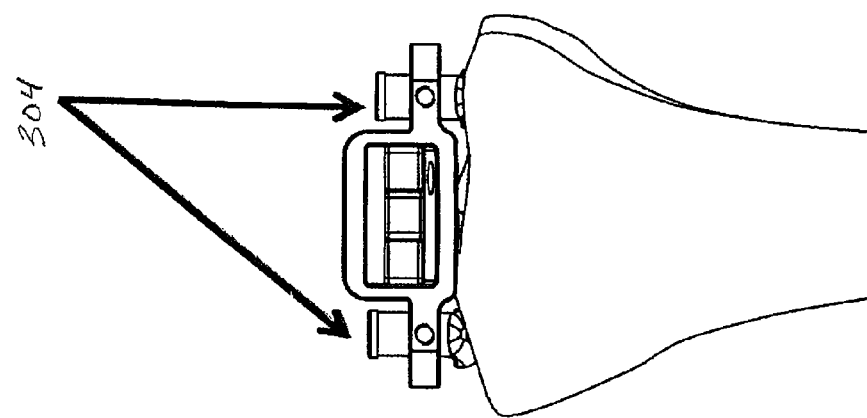
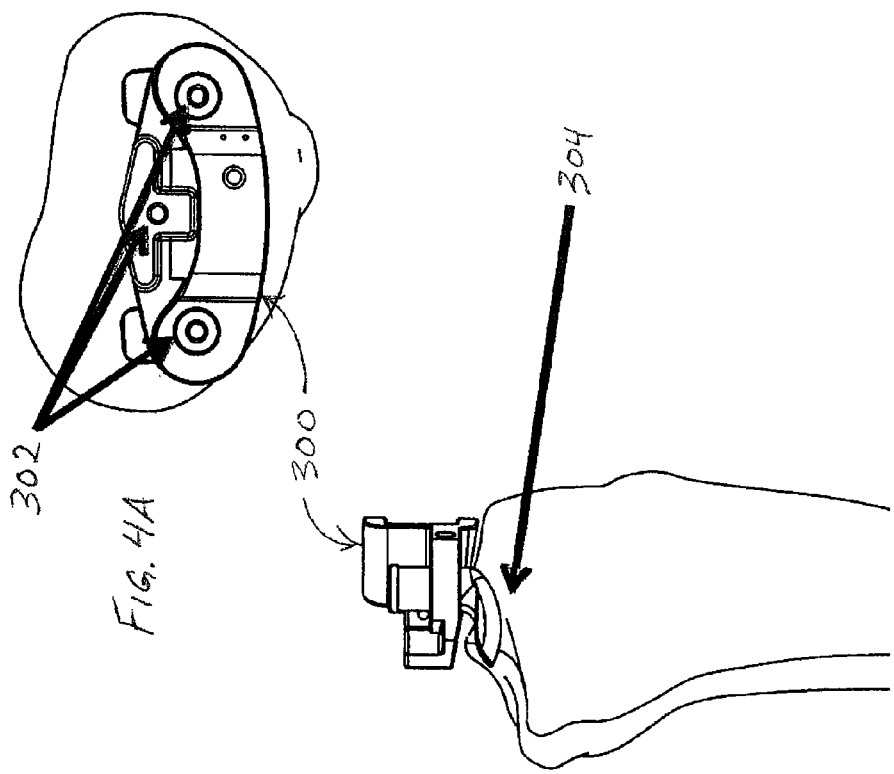

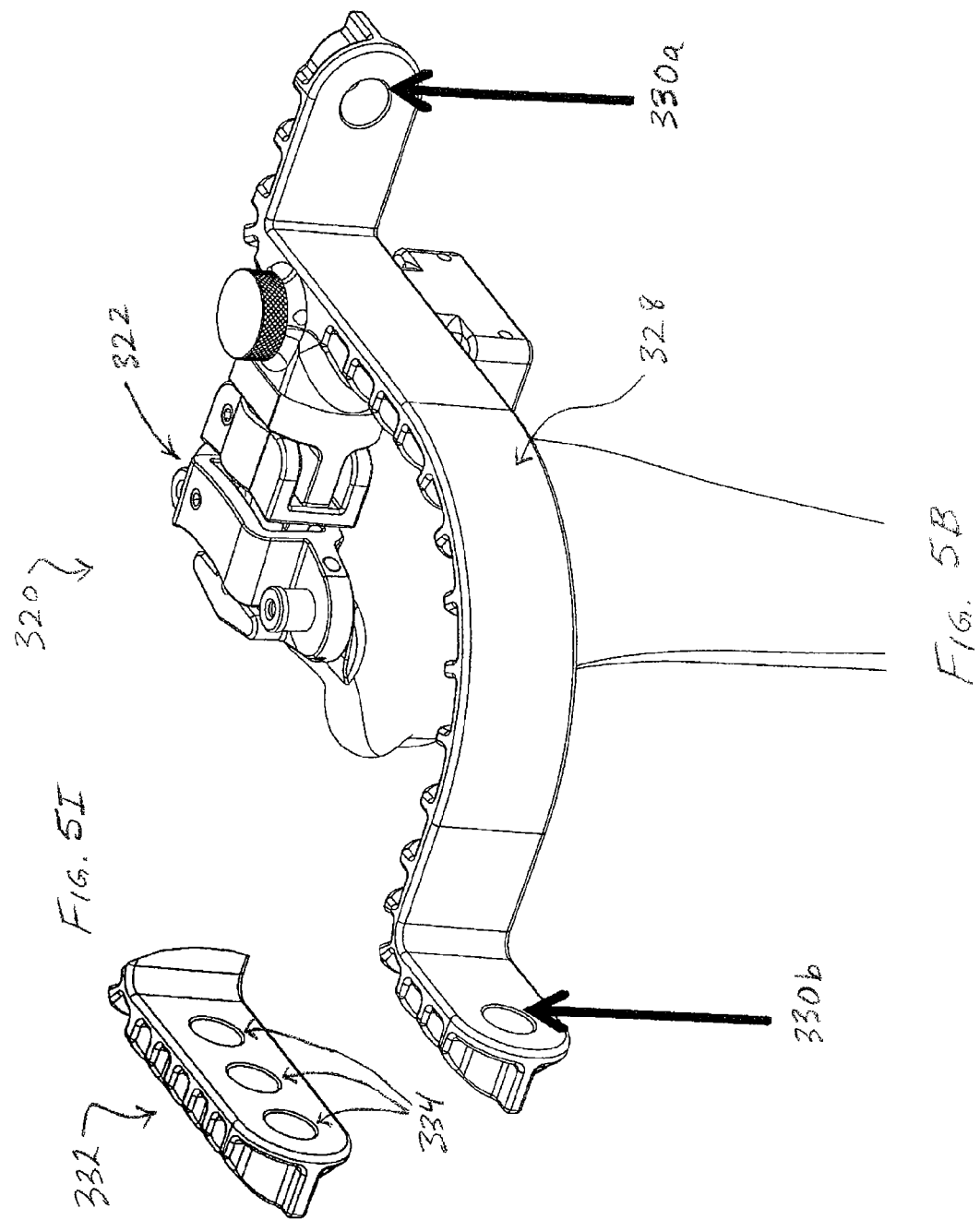

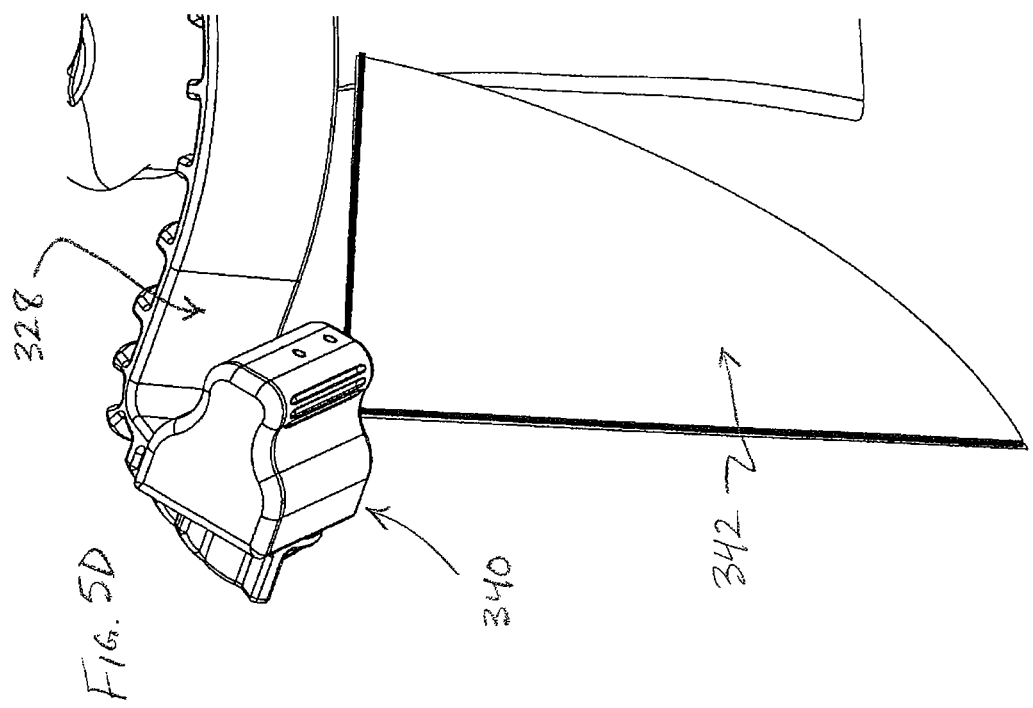
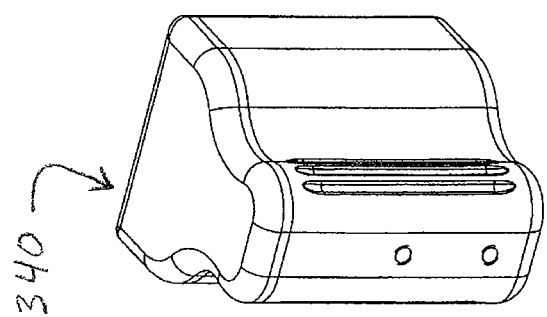

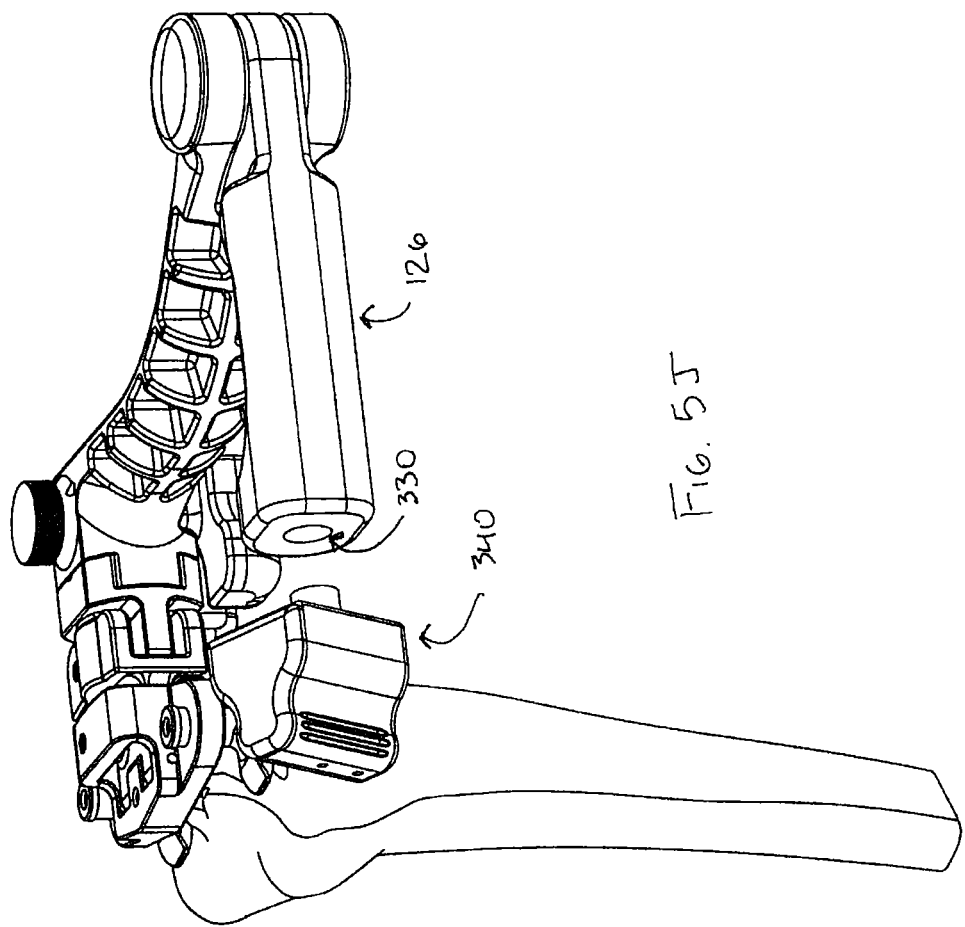

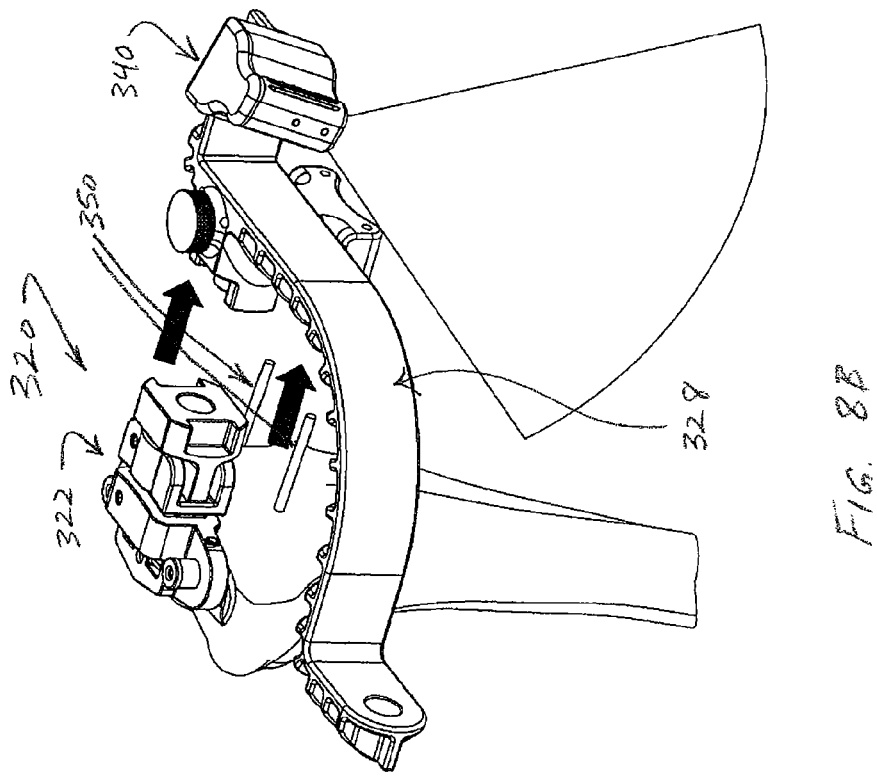
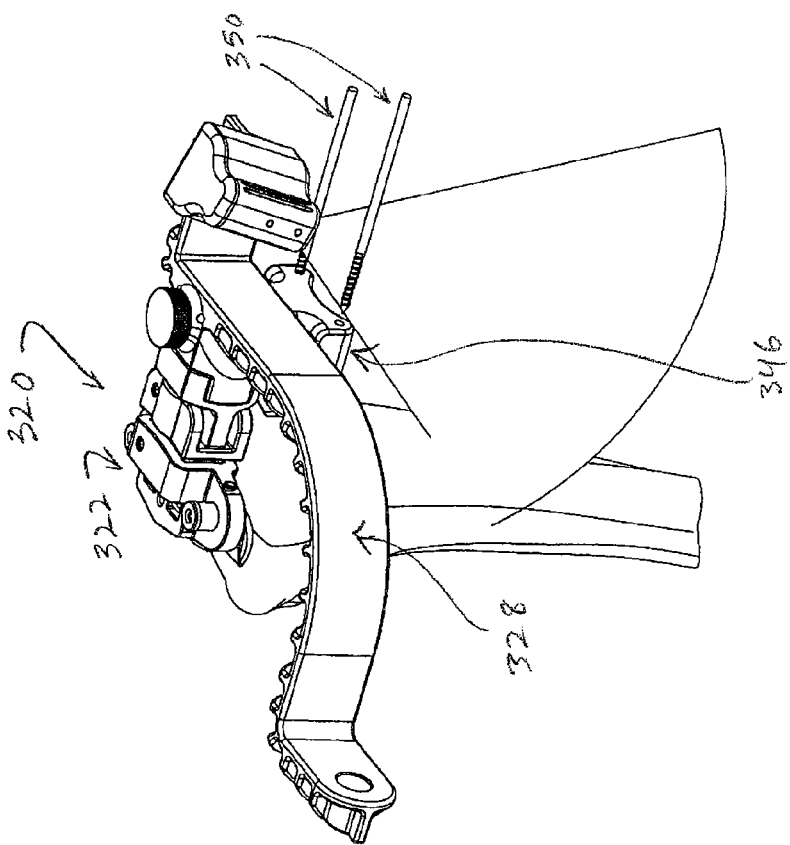

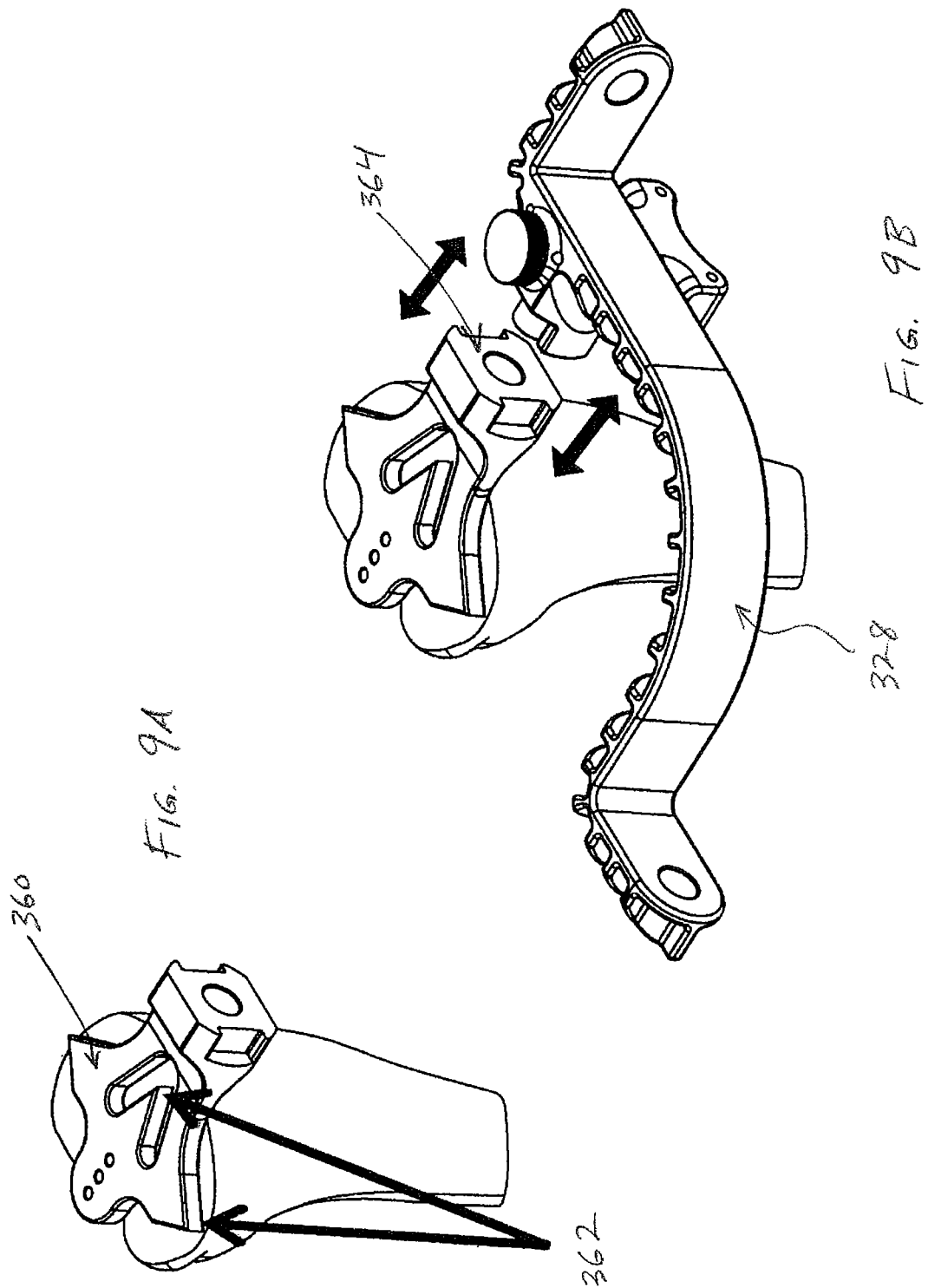

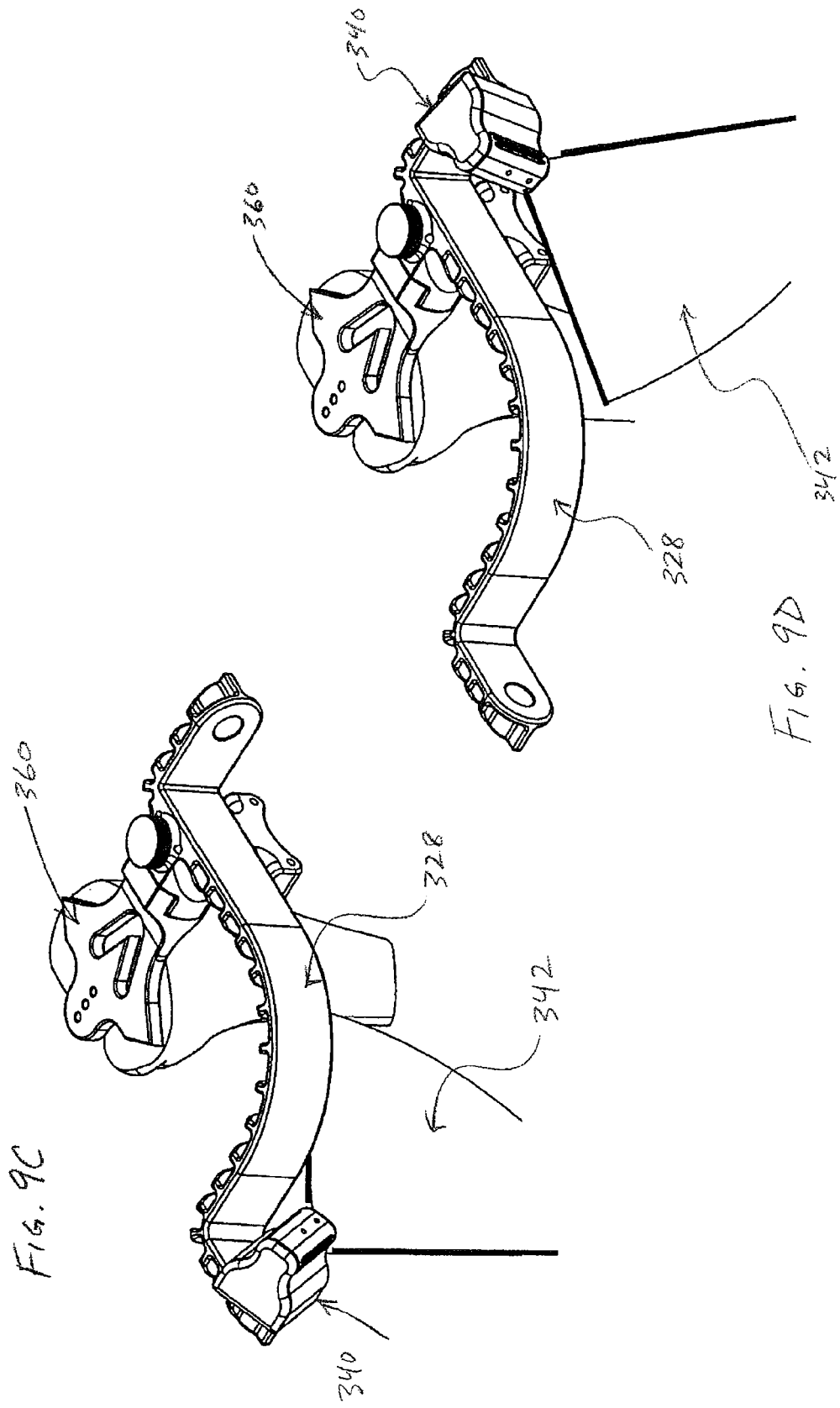

BONE POSITIONING DEVICE AND METHOD

CROSS REFERENCE TO RELATED APPLICATION

The present application is a continuation in part of U.S. patent application Ser. No. 12/616,747 filed Nov. 11, 2009 which is a continuation of PCT/US2009/063015 filed on Nov. 2, 2009, the full disclosures of which are incorporated herein by reference.

BACKGROUND

Embodiments of the here described relate to medical/surgical devices, systems and methods. More specifically, embodiments here described relate to devices, systems and methods for enhancing a knee surgery procedure.

Approximately 550,000 total knee replacement surgeries (also referred to as total knee arthroplasty ("TKA") are performed annually in the U.S. for the treatment of chronic knee pain and dysfunction. As the U.S. and world populations become older and more obese, knee replacement surgery will become even more common, as knee joints endure greater and greater wear and tear from their increased loads and years of stress. Conventional TKA surgery is often very effective but also very invasive and sometimes imprecise, thus leading to less than ideal outcomes.

The knee is generally defined as the point of articulation of the femur with the tibia. Structures that make up the knee include the distal femur, the proximal tibia, the patella, and the soft tissues within and surrounding the knee joint. Four ligaments are especially important in the functioning of the knee—the anterior cruciate ligament, the posterior cruciate ligament, the medial collateral ligament, and the lateral collateral ligament. In an arthritic knee, protective cartilage at the point of articulation of the femur with the tibia has been worn away to allow the femur to directly contact the tibia. This bone-on-bone contact causes significant pain and discomfort. The primary goals of a TKA procedure are to replace the distal end of the femur, the proximal end of the tibia, and often the inner surface of the patella with prosthetic parts to avoid bone-on-bone contact and provide smooth, well-aligned surfaces for joint movement, while also creating a stable knee joint that moves through a wide range of motion.

In a TKA surgery, the surgeon cuts open the knee, flips the patella bone out of the way, cuts bone from the distal end of the femur and from the proximal end of the tibia, and installs new, manmade, prosthetic ends onto the femur and tibia to form a new knee joint. In some TKA procedures, the interior surface of the patella may also be covered with a prosthetic. Cutting open the knee, moving the patella, sawing off bone segments, and implanting the manmade implants is a very invasive, though effective, procedure. Determining how to cut the ends of the femur and tibia to ensure proper alignment and balancing of ligament tension in the new, prosthetic knee joint can be very challenging and often involves more art than science. An artificial knee joint in which the ligament tension is not well balanced endures significantly more wear and tear than one that is properly balanced, and yet, this proper balance is very difficult to achieve. As a consequence, TKA surgery performed on younger patients typically needs to be redone one or more times during the patient's life.

Due to the invasiveness and imprecision of traditional TKA, there is a need for improved techniques and devices in this field. A number of minimally invasive (or "less invasive") TKA techniques, involving smaller incision sizes and reduced trauma to the patient have been developed in an effort to reduce patient recovery time. Some of these minimally invasive techniques, as well as other innovations, have also sought to enhance and/or facilitate TKA by making it more precise and repeatable and thus, ideally, reducing wear and tear on artificial knees and the need for repeat procedures. Improved techniques and devices would also mean enhanced outcomes for all TKA patients, with better functioning of the knee joint and longer useful life of the artificial knee.

One of the greatest challenges in TKA surgery is to properly balance ligament tension, especially in the medial and lateral collateral ligaments, through a full range of motion of the knee. The collateral ligaments, which connect the distal femur and proximal tibia on the medial and lateral aspects of the knee, account for much of the stability and movement of the knee. If one of the collateral ligaments is too lax or too tight relative to the other collateral ligament, the knee will typically be unstable, range of motion may be limited, the patella may move (or "track") improperly, and the femur and/or tibia may wear unevenly, leading to arthritis and pain. Uneven ligament tension after TKA surgery will typically cause joint instability and poor patellar tracking, limited range of motion, and impaired function of the knee, as well as uneven, increased wear of the prosthetic device, which often necessitates repeat surgery. Thus, it is imperative for the short- and long-term success of a TKA procedure to achieve balanced ligament tension in the knee through a full range of motion.

Balancing ligament tension during TKA surgery is complicated by the fact that the natural knee does not operate like a hinge moving about a single axis. The knee exhibits dynamic external rotation of the tibia relative to the femur as the knee moves from its flexed to its fully extended position. This automatic rotation of the tibia occurs in the opposite direction when the knee is flexed from its fully extended position to produce an internal rotation of the tibia relative to the femur. Thus, the natural knee exhibits a rotary laxity that allows the tibia to rotate through a limited internal and external arc during knee flexion. In addition, the femur translates anteriorly and posteriorly as the tibia is being flexed about it, bringing yet another movement variable into the equation. Thus, the ligaments of the knee, along with the femur, tibia and patella, create a truly dynamic bio-mechanism, making ligament tension balancing in TKA surgery extremely challenging. This challenge is even greater in minimally invasive TKA procedures, in which incisions are smaller than those made in "open" TKA surgeries. Additionally, the incision made during minimally invasive TKA surgery is biased to the medial side, leaving the lateral side of specifically the distal femur "closed" to access of front or end loaded surgical instruments One way surgeons try to balance ligament tension during TKA procedures is by cutting one or more ligaments to release tension from one part of the joint ("ligament release"). The disadvantage of ligament release, however, is that once a ligament is cut it cannot be regenerated, and the ligaments of the knee provide much needed stability to the knee joint.

Rather than or in addition to ligament release, the components of a total knee prosthesis may be selected and positioned to balance ligament tension. Since the femoral and tibial components of the knee prosthesis are attached to cut surfaces of the distal femur and proximal tibia respectively, placement and orientation of the femoral and tibial bone cuts are very important for balancing knee ligament tension. As with ligament release however, it is often very challenging to position the femoral and tibial bone cuts and prosthetic components to provide ideal ligament tension through the range of motion. This is due primarily to the complexity of motion about the knee, as described above, and the difficulty of assessing and making the bone cuts during the procedure to achieve desired ligament tension through the full range of motion.

Improved methods and apparatus for facilitating and/or enhancing femoral bone cuts have been described by the assignee of the present application in, for example, U.S. Pat. Nos. 7,578,821 and 7,442,196. Few if any innovations have been made, however, to facilitate or enhance tibial bone cuts in a TKA procedure.

To make a tibial cut in a typical TKA procedure, an orthopedic surgeon typically uses a cutting block or cutting guide temporarily attached to the front of the tibia via a rod that is typically attached to an ankle clamp at the distal end to the tibia (an extramedulary rod) and aligned approximately with the mechanical axis of the anterior surface of the tibia. The cutting block is used to guide a surgical saw blade or rotary tool in making the tibial bone cut. Positioning such a cutting block, therefore, is crucial to forming well-positioned bone cuts for attachment of the tibial and femoral prosthetic components. The tibial cut is the foundation of a TKA, as it affects the spacing, alignment and balance between the tibia and femur when the knee is in flexion (the flexion gap) the spacing, alignment and balance between the tibia and femur when the knee is in extension (the extension gap) and all points of articulation between extension and flexion. Typically, the tibial component of a knee prosthesis is positioned on a flat, horizontal cut surface of the proximal tibia (at a 90 degree "varus/valgus" angle relative to the long axis of the tibia), and the position and orientation of the tibial component typically do not vary greatly from knee to knee. However, by making a cut on the tibia at 90 degrees to the long axis of the bone, a bigger space is created laterally than medially, due to the tibia's natural approximately 3 degrees of varus slope. Furthermore, the "classic" 90-degree tibial bone cut is typically made by the surgeon simply approximating the 90-degree angle. Therefore, the usual cut made to the tibia in TKA is not necessarily ideal and is made by approximation. Thus, improvements to the angle and precision of the tibial cut may improve the ligament balancing and overall result of a TKA procedure.

Therefore, a need exists for improved devices, systems and methods for enhancing TKA surgery and specifically for enhancing and/or facilitating the positioning of one or more tibial bone cuts made during a TKA procedure to accommodate a tibial prosthetic. Ideally, such devices, systems and methods would allow a physician to effectively select an angle at which to make a tibial bone cut and would help the physician more accurately make the cut at the selected angle. Such devices, systems and methods would also ideally be simple to use in conjunction with cutting guides, saw blades or burs, robotic and navigational systems, and/or any other equipment used by a surgeon in a TKA procedure. At least some of these objectives will be met by various embodiments of present invention.

BRIEF SUMMARY

The present invention relates to knee arthroplasty apparatus and method. The present invention provides devices, systems and methods for positioning a bone cut which may be a bone cut on a tibia as part of a TKA or other knee surgery procedure. These devices, systems and methods generally help a physician achieve balancing of ligaments during the knee surgery procedure, thus potentially enhancing the outcome of the procedure and/or reducing wear and tear of an artificial knee joint implanted during the procedure.

In one aspect, a method for positioning a bone cutting guide may involve coupling a cutting guide positioning apparatus with a tibia, adjusting the positioning apparatus in a varus/valgus orientation, adjusting the positioning apparatus in an anterior/posterior orientation, adjusting the positioning apparatus up or down to select a tibial bone resection level, and contacting a cutting guide with the tibia, using the adjusted positioning apparatus. In some embodiments, the method may further include emitting light in a linear configuration from the cutting guide positioning device. In such embodiments, adjusting the apparatus in the varus/valgus orientation may involve moving the light to shine along approximately a midline of an anterior surface of the tibia, and adjusting the apparatus in the anterior/posterior orientation may involve moving the light to shine along approximately a midline of a side of the tibia. In one embodiment, the side of the tibia along which light is shone is the medial side. Optionally, this method may further involve swinging a swing arm of the cutting guide positioning apparatus approximately 90 degrees between the steps of adjusting in the varus/valgus orientation and adjusting in the anterior/posterior orientation. One embodiment further involves locking in the varus/valgus orientation before swinging the swing arm.

In some embodiments, the cutting guide is removably coupled with the guide positioning apparatus during the adjusting steps. In some embodiments, the method further includes attaching the cutting guide to the tibia. Optionally, the method may further include removing the positioning apparatus from the tibia and the cutting guide and making at least one cut on the tibia guided by the cutting guide.

In one embodiment, adjusting the positioning apparatus up or down to select a tibial bone resection level involves moving a resection level adjustment member up or down to contact a stylus touching an upper surface of the tibia and extending to a location anterior to and below the upper surface. In the present application, the "upper surface" of the tibia means the superior articular surface (or surfaces) of the tibia before any tibial bone cuts have been made. These superior surfaces are often referred to as the medial and lateral articular surfaces or the medial and lateral facets of the tibia. For the purposes of this application, any of the terms "upper surface," "articular surface," "facet" or "extreme proximal end" of the tibia may be used interchangeably. In one embodiment, the location anterior to and below the upper surface is between about 8 mm and about 11 mm below the upper surface, and the upper surface is the lateral articular surface of the tibia.

In some embodiments, coupling the cutting guide positioning apparatus with the tibia involves advancing the at least one hole in the apparatus over at least one reference pin attached to the tibia. In one embodiment, two foot pads of the positioning device are advanced over two reference pins to contact the medial and lateral articular surfaces of the tibia.

In another aspect, a method for positioning a bone cutting guide on a tibia may include: coupling a cutting guide positioning apparatus with a tibia, wherein the positioning apparatus is coupled with a tibial cutting guide; emitting a light from the positioning apparatus; adjusting the positioning apparatus in a varus/valgus orientation to shine the light approximately along a midline of an anterior surface of the tibia; swinging a swing arm of the positioning apparatus approximately 90 degrees to shine the light along a side of the tibia; adjusting the positioning apparatus in an anterior/posterior orientation to shine the light approximately along a midline of the side of the tibia; adjusting the positioning apparatus up or down to select a tibial bone resection level; and attaching the tibial cutting guide to the tibia, using the adjusted positioning apparatus.

In another aspect, a device for positioning a bone cut on a tibia may include: a tibial attachment member; a coupler moveably attached to the tibial attachment member; a rotationally moveable arm rotationally attached to the coupler; a swing arm coupled with the rotationally moveable arm via an axle such that a free end of the swing arm swings from an anterior position to a side position; a light emitting member coupled with the swing arm at or near the free end for emitting light along the tibia; a varus/valgus adjustment member for adjusting the rotationally moveable arm to direct the emitted light approximately along a midline of an anterior surface of the tibia; an anterior/posterior adjustment member for adjusting the coupler in an anterior/posterior orientation relative to the tibial attachment member to direct the emitted light approximately along a midline of a side of the tibia; and a tibial bone resection level adjustment member for selecting a level for resecting the tibia.

In some embodiments, the tibial attachment member may include at least one foot pad for contacting an articular surface of an uncut tibia and at least one hole for passing the attachment member over a reference pin attached to the tibia. In one embodiment, the attachment member includes a medial articular surface footpad having a first hole and a lateral articular surface footpad having a second hole.

In some embodiments, the light emitting member emits light in a linear or planar configuration. The side of the tibia is the medial side in some embodiments, and the swing arm rotates between a first position in which the light shines along the anterior surface of the tibia and a second position in which the light shines along the medial side of the tibia. Alternatively, the lateral side of the tibia may be addressed in other embodiments. Some embodiments may further include a stylet coupled with the tibial attachment member and configured to extend from an upper surface of the tibia to a location anterior to and below the upper surface. This tibial bone resection level adjustment member is adjustable to contact the tibial cutting guide with the stylus at the location. In some embodiments, the device further includes a tibial cutting guide holder, where adjustments of the adjustment members adjust a position of the cutting guide holder.

In another aspect, a system for positioning a tibial cutting guide on a tibia may include a tibial cutting guide and a cutting guide positioning device. The positioning device may include: a tibial attachment member; a coupler moveably attached to the tibial attachment member; a rotationally moveable arm rotationally attached to the coupler; a swing arm coupled with the rotationally moveable arm via an axle such that a free end of the swing arm swings from an anterior position to a side position; a light emitting member coupled with the swing arm at or near the free end for emitting light along the tibia; a varus/valgus adjustment member for adjusting the rotationally moveable arm to direct the emitted light approximately along a midline of an anterior surface of the tibia; an anterior/posterior adjustment member for adjusting the coupler in an anterior/posterior orientation relative to the tibial attachment member to direct the emitted light approximately along a midline of a side of the tibia; a tibial bone resection level adjustment member for selecting a level for resecting the tibia; and a tibial cutting guide holder, where adjustments of the adjustment members adjust a position of the cutting guide holder.

Generally, the tibial cutting guide holder is moveable relative to the rotationally moveable arm to move the tibial cutting guide into contact with the tibia. In some embodiments, the system may further include at least one reference pin for removably attaching the tibial attachment member of the guide positioning device to the tibia. Optionally, the system may further include at least one cutting guide fastener, such as a pin or rod, for attaching the tibial cutting guide to the tibia.

In another aspect, a method for positioning a bone cut on a tibia may involve: coupling a bone cut positioning apparatus with a tibia; adjusting the positioning apparatus in a varus/valgus orientation relative to the tibia; adjusting the positioning apparatus in an anterior/posterior orientation relative to the tibia; and adjusting the positioning apparatus up or down to select a tibial bone resection level. Optionally, the method may further include, before adjusting in the varus/valgus orientation, attaching a laser light emitter to an arm of the positioning apparatus and, before adjusting in the anterior/posterior orientation, detaching the laser light emitter from the arm and reattaching it at or near an opposite end of the arm. In such an embodiment, attaching the emitter to the positioning apparatus activates the emitter such that it can emit laser light, adjusting the apparatus in the varus/valgus orientation comprises moving emitted laser light to shine along approximately a midline of an anterior surface of the tibia, and adjusting the apparatus in the anterior/posterior orientation comprises moving emitted laser light to shine along approximately a midline of a side of the tibia. In some embodiments, the side of the tibia is the medial side.

In one embodiment, coupling the bone cut positioning apparatus with the tibia may involve coupling a tibial attachment member with a proximal end of the tibia and coupling the arm of the positioning apparatus with the tibial attachment member. The arm extends around the tibia approximately 90 degrees from a first end of the arm anterior to the tibia to a second end of the arm lateral or medial to the tibia. In one embodiment, the arm may attach to the tibial attachment member via magnetic connection and the laser light emitter attaches to the arm via magnetic connection.

Also in one exemplary embodiment, the adjusting steps comprise adjusting a screw coupled with a captured ball to move a portion of the positioning apparatus about a pivot. The method may optionally further involve using the positioning apparatus to attach a bone cutting guide to the tibia. In such an embodiment, the method may further involve removing the positioning apparatus from the tibia and the cutting guide and making at least one cut on the tibia guided by the cutting guide.

In another aspect, a method for positioning a bone cut on a tibia may involve: coupling a bone cut positioning apparatus with a tibia; coupling a laser light emitter with the positioning apparatus at or near one end of an arm of the apparatus, such that when the emitter is coupled with the apparatus is emits light; adjusting the positioning apparatus in a varus/valgus orientation to shine the emitted light approximately along a midline of an anterior surface of the tibia; coupling the laser light emitter with the positioning apparatus at or near an opposite end of the arm, such that when the emitter is coupled with the apparatus is emits light; adjusting the positioning apparatus in an anterior/posterior orientation to shine the light approximately along a midline of a side of the tibia; and adjusting the positioning apparatus up or down to select a tibial bone resection level. Optionally, in one embodiment the method may also include attaching a tibial cutting guide to the tibia, using the adjusted positioning apparatus, removing the positioning apparatus from the tibia and the cutting guide, and making at least one cut on the tibia guided by the cutting guide.

In yet another aspect of the present invention, a device for positioning a bone cut on a tibia may include a tibial attachment member, an arm attachable to the tibial attachment member and extending in an arc of approximately 90 degrees, a laser light emitter attachable to the arm at a first position at or near one end of the arm an a second position at or near an opposite end of the arm, a varus/valgus adjustment member for moving the arm to direct light emitted by the emitter in the first position approximately along a midline of an anterior surface of the tibia, an anterior/posterior adjustment member for moving the arm to direct light emitted by the emitter in the second position approximately along a midline of a side of the tibia, and a bone resection level adjustment member for selecting a level for resecting the tibia.

In some embodiments, the tibial attachment member may include independently movable medial and lateral feet for contacting the medial and lateral articular surfaces of the tibia. In one embodiment, the varus/valgus adjustment member comprises a first captured ball and captured screw that rotates the tibial attachment member about a first pivot point, and the anterior/posterior adjustment member comprises a second capture ball and captured screw that rotates the tibial attachment member about a second pivot point. In one embodiment, the laser light emitting member attaches to the arm at the first position and the second position via magnetic force. In this or other embodiments, the arm may attach to the tibial attachment member via magnetic force.

One embodiment may further include a tibial cutting guide holder, wherein adjustments of the adjustment members adjust a position of the cutting guide holder. Some embodiments may further include a depth gauge coupled with the bone resection level adjustment member.

In another aspect of the invention, a system for positioning a bone cut on a tibia may include a tibial cutting guide and a bone cut positioning device. The cutting guide positioning device may include: a tibial attachment member; an arm attachable to the tibial attachment member and extending in an arc of approximately 90 degrees; a laser light emitter attachable to the arm at a first position at or near one end of the arm an a second position at or near an opposite end of the arm; a varus/valgus adjustment member for moving the arm to direct light emitted by the emitter in the first position approximately along a midline of an anterior surface of the tibia; an anterior/posterior adjustment member for moving the arm to direct light emitted by the emitter in the second position approximately along a midline of a side of the tibia; and a bone resection level adjustment member for selecting a level for resecting the tibia.

In one embodiment, the tibial cutting guide holder is moveable relative to the arm to move the tibial cutting guide into contact with the tibia. Optionally, the system may further include at least one reference pin for removably attaching the tibial attachment member of the guide positioning device to the tibia. The system may also include at least one cutting guide fastener for attaching the tibial cutting guide to the tibia. In some embodiments, the laser light emitting member emits light in a linear or planar configuration that may be directed along the tibia. In some embodiments, the laser light emitting member attaches to the arm at the first position and the second position via magnetic force. In some embodiments, the arm attaches to the tibial attachment member via magnetic force. Some embodiments may further include a depth gauge attachable to the cutting guide positioning device. In some embodiments, the depth gauge comprises a slidable member adjustable by moving the bone resection level adjustment member and including at least one indicator to indicate to a user when a desired bone cut level has been reached. In some embodiments, the at least one depth gauge comprises multiple depth gauges provided as a set, each gauge having an indicator at a different depth for facilitating a different bone resection level. For example, in one embodiment, the multiple depth gauges comprise three gauges having indicators at 3 mm, 9 mm and 10 mm of depth. In various embodiments, the indicator on a depth gauge may include but is not limited to an LED, a colored marker, a reflective marker and/or a tactile element.

For a further understanding of the nature and advantages of the invention, reference should be made to the following description taken in conjunction with the accompanying figures. However, each of the figures is provided for the purpose of illustration and description only and is not intended to limit the scope of the embodiments of the present invention.

BRIEF DESCRIPTION OF THE DRAWINGS

FIGS. 4A-4I are various views of a tibial attachment member of a bone cut positioning system according to one embodiment;

FIGS. 5A-5J are various views of a bone cut positioning system according to an alternative embodiment;

FIGS. 8A-8D demonstrate a method for placing guide pins and a guide block using a bone cute positioning system according to one embodiment;

FIGS. 9A-9D are various views of a tibial cut check device according to one embodiment;

DETAILED DESCRIPTION OF THE INVENTION

The devices, systems and methods described below may be used in various embodiments to enhance and/or facilitate a total knee arthroplasty (TKA) procedure, a partial knee arthroplasty procedure, or any other suitable knee surgery procedure in which one or more cuts are made on a tibia, typically a proximal end of a tibia. Generally, the embodiments described herein provide a means for positioning a bone cut on a tibia. Although the following description may frequently refer to TKA procedures, the described embodiments may also be used for partial knee arthroplasty procedures or other knee procedures in which tibial bone cuts are made.

Figure 1A:
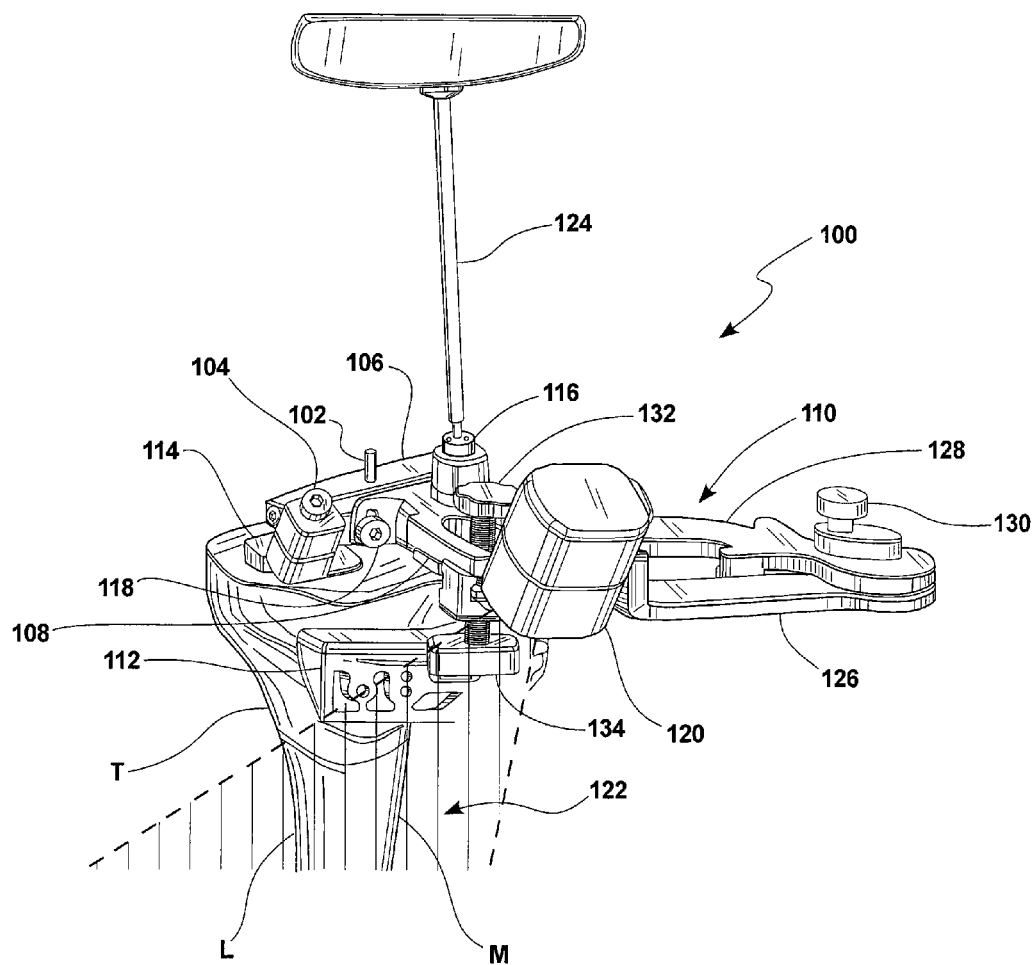
FIG. 1A is a perspective view of a bone cut positioning system coupled with a proximal end of a tibia, according to one embodiment.

Referring to FIG. 1A, one embodiment of a bone cut positioning system 100 is shown attached to a tibia T. In this view, the tibia T is of a right leg and is in an anterior (front) facing orientation, with the lateral side L of the tibia T toward the left side of the figure and the medial side M of the tibia toward the right side of the figure.

Figure 1B:
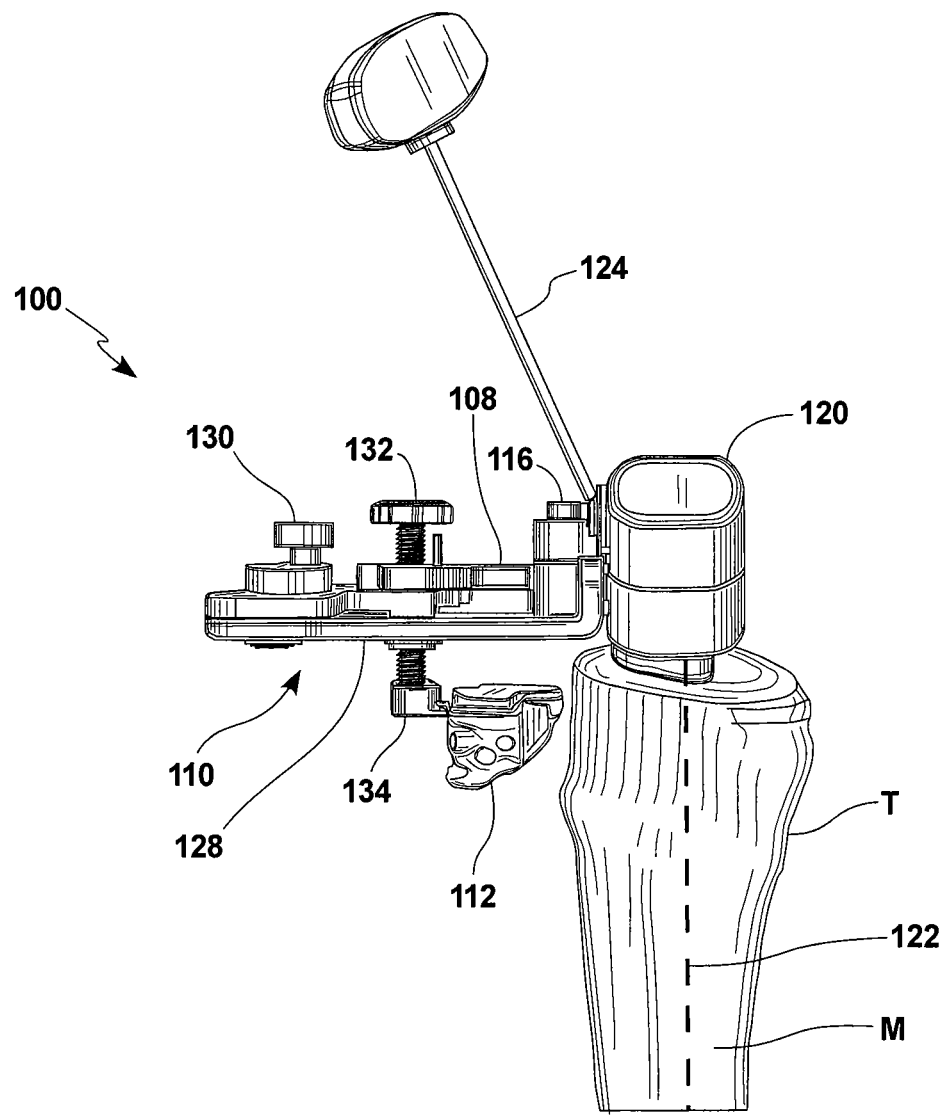
FIG. 1B is a side view of the system and tibia of FIG. 1A.
Figure 1C:
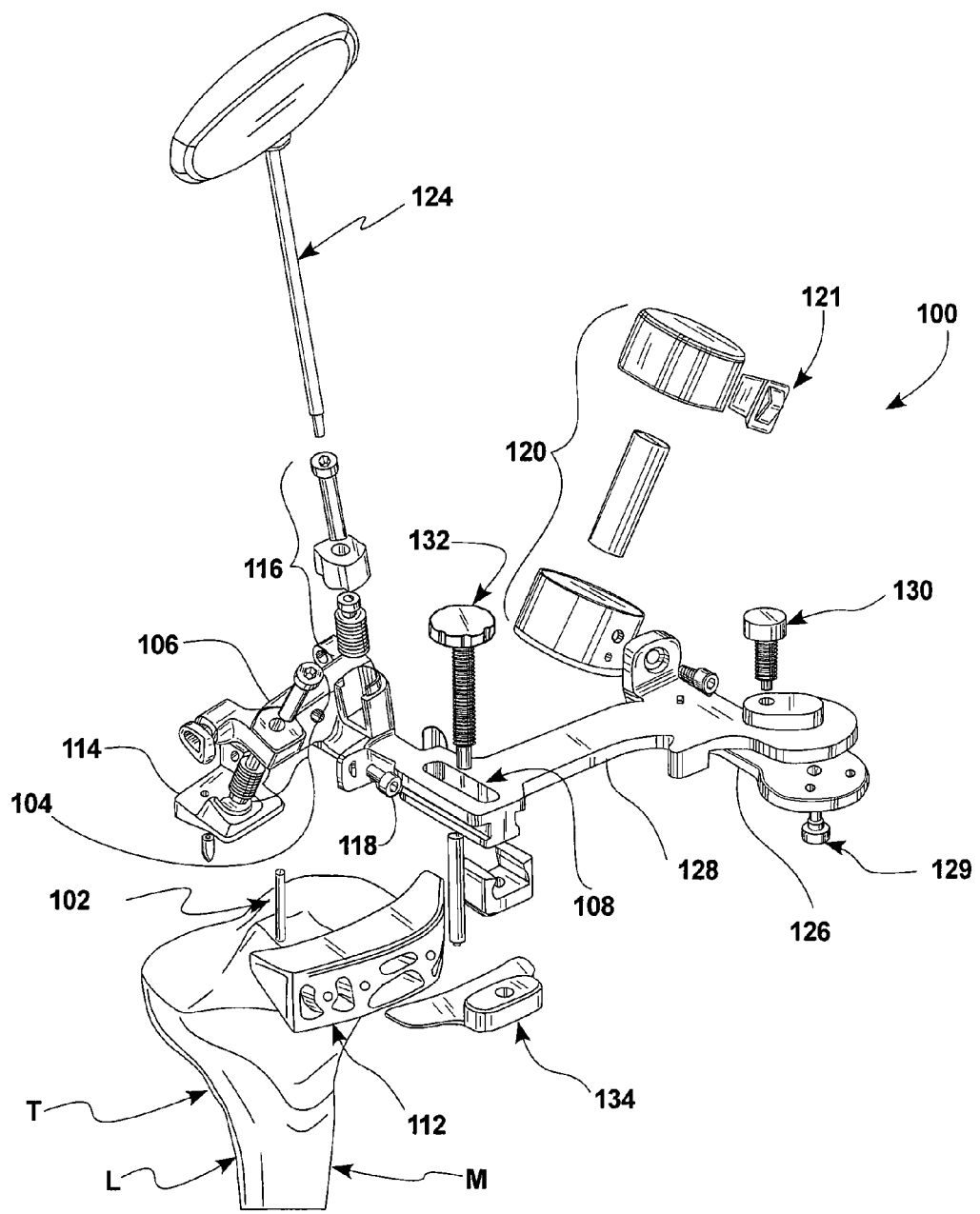
FIG. 1C is an exploded perspective view of the system of FIGS. 1A and 1B.

FIG. 1B shows system 100 in place with the medial side M of the tibia T facing out of the page and the system 100 rotated to address the medial side M, as will be explained in more detail below. FIG. 1C shows an exploded view of system, and FIG. 1D shows an exploded view of part of system 100.

In the embodiment of FIGS. 1A-1D, system 100 for enhancing and/or facilitating positioning a bone cut on a tibia T includes a bone cutting guide 112 (or "guide block") and a bone cut positioning device 110. In alternative embodiments, positioning device 110 may be adapted to position a bone cut without using cutting guide 112, or by using a different variation of cutting guide 112. In various embodiments, bone cutting guide 112 may be any currently available or subsequently developed bone cutting guide 112. Because bone cutting guides or guide blocks are well known in the art, they will not be described further herein. In various embodiments, bone cutting guide 112 may be provided as part of the system 100 or alternatively may be available separately.

In some embodiments, bone cut positioning device 110 may be coupled to the tibia T via a tibial reference pin 102 (or "tibial pin") inserted into the tibia T. Pin 102 may be part of system 100 or may be available separately, in various embodiments. Pin 102 may be used in place of extramedulary rods.

Figure 1D:
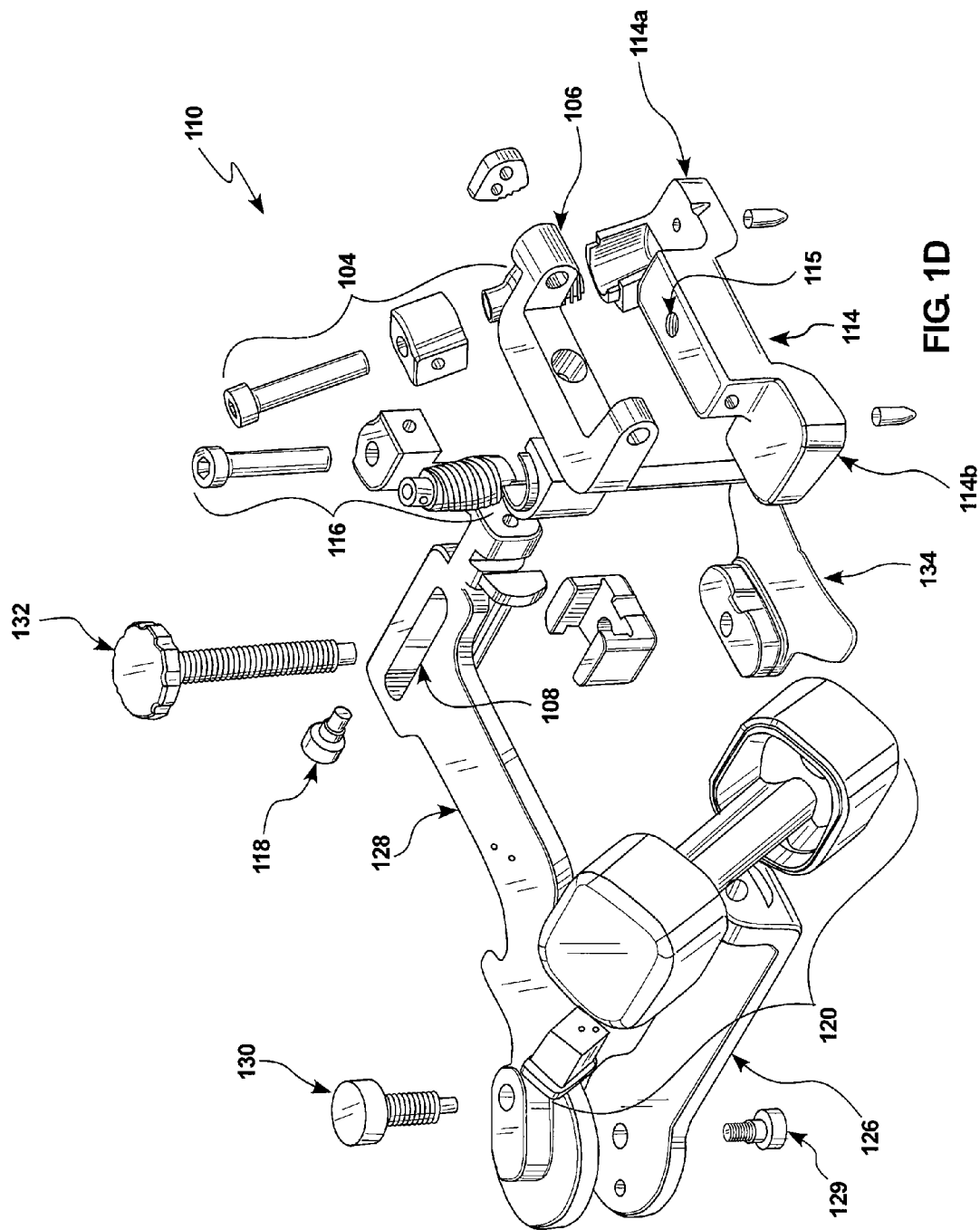
FIG. 1D is an exploded view of a portion of the system of FIGS. 1A-1C.

In the embodiment of FIGS. 1A-1D, bone cut positioning device 110 includes a number of component parts, some of which may be more easily viewed in FIGS. 1C and 1D. As shown in FIG. 1D, for example, positioning device 110 may include a tibial attachment member 114 that attaches directly to the tibia T via a hole 115 for accepting pin 102 and is rotationally moveable relative to the tibia T during use of positioning device 110. In this embodiment, tibial attachment member 114 includes two foot pads—a right foot pad 114a and a left footpad 114b—for contacting the proximal end of the tibia T. In alternative embodiments, one foot pad or more than two foot pads may be used. Positioning device 110 also includes a coupler 106, which attaches a rotationally moveable arm 128 to tibial attachment member 114. A varus/valgus adjustment member 116 and an anterior/posterior adjustment member 104 (or "tibial slope adjustment member") move members 128 and 106 relative to the tibial attachment member 114 to adjust the orientations of device 110 and thus adjust the orientation of cutting guide 112 relative to the tibia T. In the embodiment shown, adjustment members 116, 104 are threaded, bolt-like apparatus that are adjustable by an adjustment device 124, such as but not limited to the Allen wrench shown in the figure. In alternative embodiments, any other suitable adjustment apparatus may be used for adjusting coupler 106 relative to tibial attachment member 114, such as rack and pinion gears, ring and pinion gears or the like.

Rotationally moveable arm 128 may be rotated during a positioning process by adjusting adjustment member 116, though rotationally moveable arm 128 remains anterior to the tibia T during the positioning procedure. Rotationally moveable arm 128 includes a slot 108 for receiving a tibial bone resection level adjustment member 132, which is coupled with a cutting guide attachment member 134, which in turn is removably coupled with cutting guide 112. In one embodiment, tibial bone resection level adjustment member 132 may comprise a bolt-like apparatus with threads and an adjustment knob, as pictured in FIGS. 1A-1D. Slot 108 is configured to allow resection level adjustment member 132 to slide horizontally back and forth to move cutting guide 112 toward and away from the tibia T and to move vertically up and down to select a height (i.e., bone resection level) at which cutting guide 112 will create a bone resection plane to be established by a saw blade upon the tibia T. In some embodiments, resection level adjustment member 132 may be locked or set at a desired level after adjustment.

Rotationally moveable arm 128 is coupled with a swing arm 126 (or "swivel arm") at a pivot point via an axle 129. Optionally, a lock screw 130 may be included to lock swing arm 126 relative to rotationally moveable arm 128, typically in either a 0° (facing anterior tibia) or a 90° (facing side tibia) orientation. Swing arm 126, in turn, is coupled with a light emitting apparatus 120, generally including a light source and in some embodiments an on/off switch 121. Light emitting apparatus 120 is capable of directing a plane of light 122 (FIGS. 1A and 1B) toward a surface of a tibia T for guiding orientation and adjustment of device 110. In alternative embodiments, the light emitted by light emitting apparatus may be in the form of a beam, fan, or any other suitable linear configuration for shining along a length of a tibia. In some embodiments, light emitting apparatus 120 may be tilted by a user to ensure that the plane of light 122 is directed along the tibial surface.

Swing arm 126 may be configured to rotate from the 0° position toward either side to the 90° position. In one embodiment, for example, swing arm 126 may be rotated from the 0° position to a 90° position facing a medial side of a tibia on a first knee of a patient and may be rotated in the opposite direction on the second knee of the patient so that the 90° position also faces the medial side of that second tibia. In alternative embodiments, the 90° position may be either a medial side or a lateral side of a tibia.

Coupler 106 may be adjusted in the anterior/posterior orientation via adjustments to an anterior/posterior adjustment member 104. In various embodiments, coupler 106 may be locked in the anterior/posterior orientation as well as or alternative to locking in the varus/valgus orientation. In some embodiments, adjustment members 116, 104 and locking member 118 may all be screws, bolts or other threaded adjustment members. In the embodiment shown, adjustment members 116, 104 and locking member 118 are adjusted using Allen wrench 124, although in alternative embodiments any suitable adjustment device may be used, such as a screw driver, wrench, fingers or the like.

Referring to FIGS. 1C and 1D, tibial bone resection adjustment member 132 passes through slot 108 and attaches to cutting guide attachment member 134. Cutting guide attachment member 134 is configured as a platform for holding cutting guide 112. In alternative embodiments, attachment member 134 may have any other suitable shape, size or configuration for removably coupling with one or various different cutting guides.

The various components of bone cut positioning device 110 may be manufactured from any suitable materials. For example, in some embodiments many of the components may be made of stainless steel or other metal, which other components may be plastic. In a typical embodiment, all materials of device 110 may be sterilizable by commonly used sterilization techniques, such as gamma irradiation, EtO sterilization and the like. Any adjustment screws, bolts, trunions or the like may be substituted with similar adjustment means in alternative embodiments, and adjustment devices such as Allen wrenches, screw drivers and the like may be likewise substituted.

Referring now to FIGS. 2A-2J, a method is shown for positioning a bone cut on a tibia as part of a TKA or other knee surgery procedure according to one embodiment. As shown in a perspective view in FIG. 2A, bone cut positioning system 100 (bone cut positioning device 110 and cutting guide 112) may first be coupled with the tibia T via reference pin 102. When initially attached, bone cut positioning device 110 may be adjusted such that swing arm 126 positions light emitting device 120 at the 0° angle, i.e., facing the anterior surface of the tibia T. Plane of light 122 may be generally directed toward the anterior surface of the tibia T but may not be initially aligned to shine directly along the midline of the anterior surface.

Figure 2A:
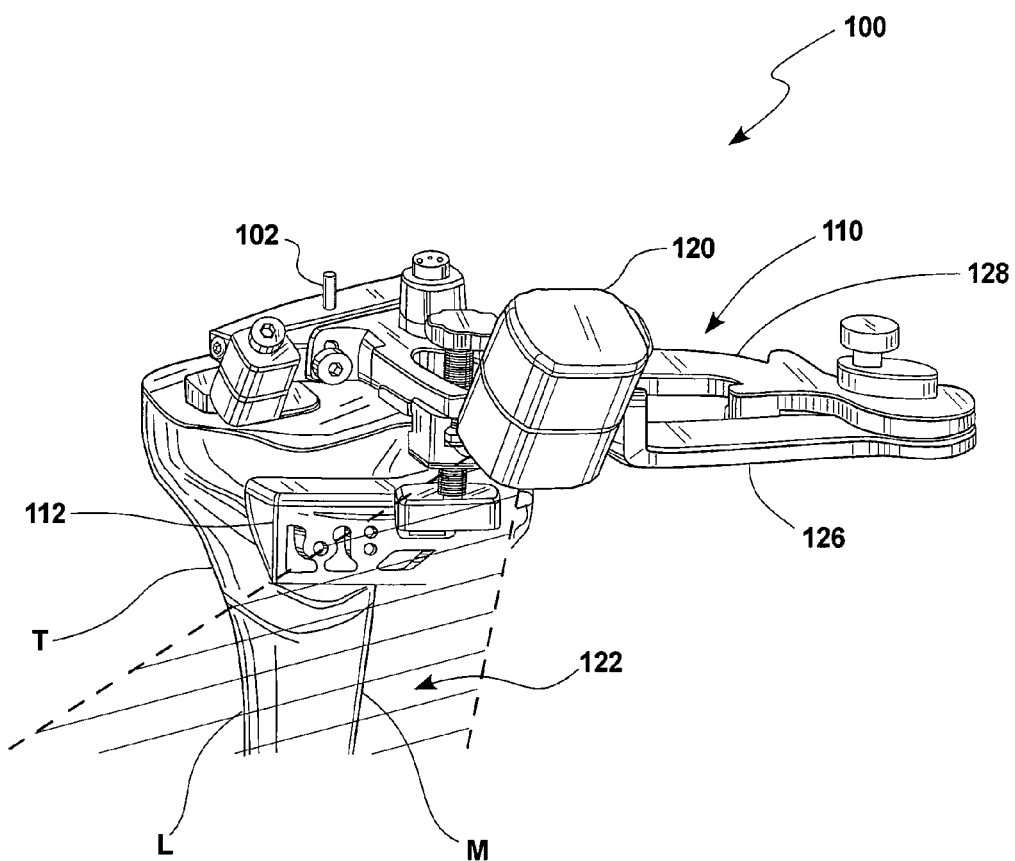
FIGS. 2A-2J illustrate a method for positioning a bone cut using a bone cut positioning system, according to one embodiment.
Figure 2B:
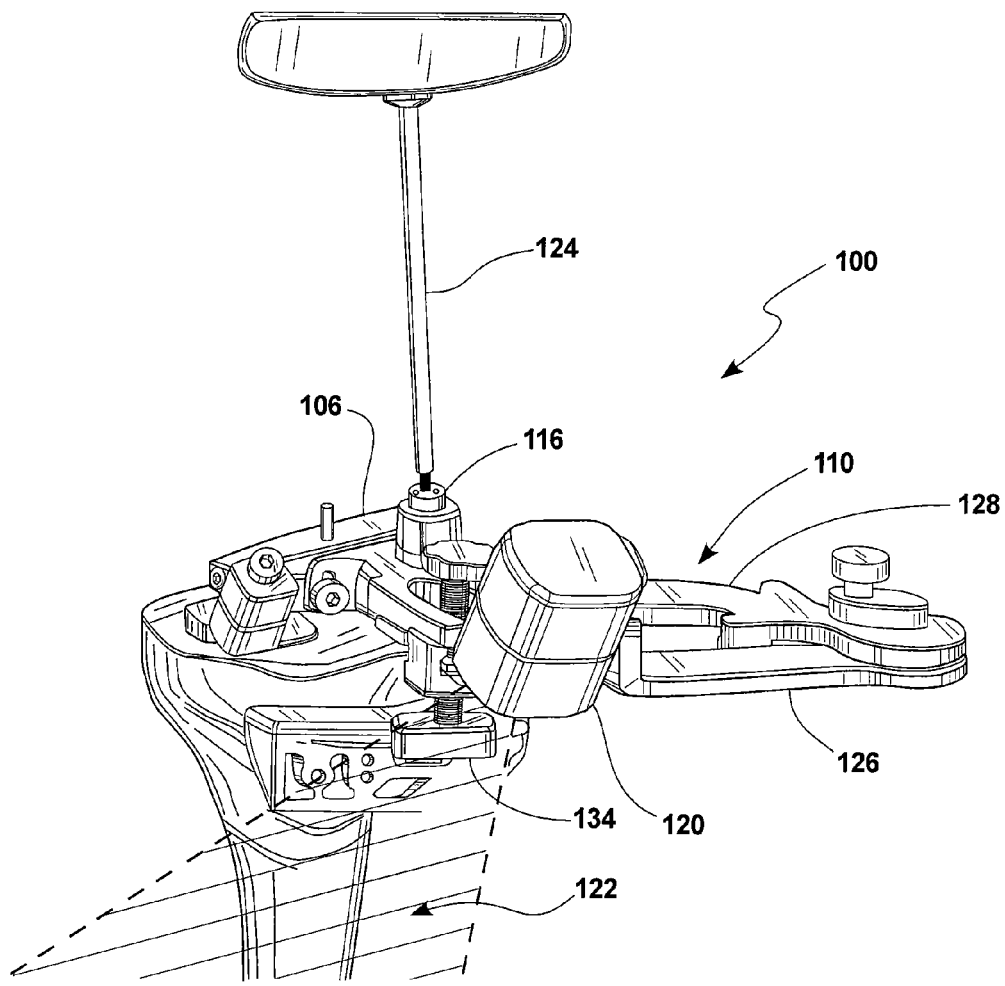
Figure 2C:
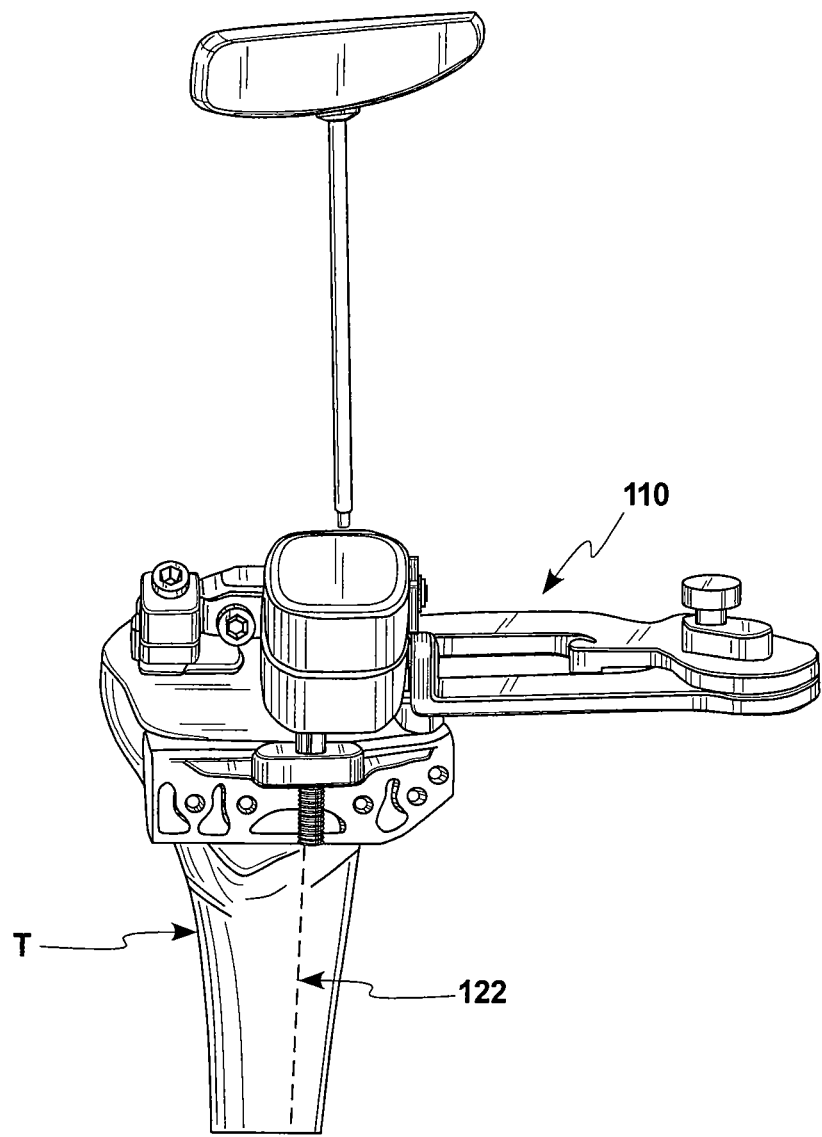

As shown in FIGS. 2B and 2C, adjustment device 124 may be used to adjust varus/valgus adjustment member 116, which in turn moves rotationally moveable arm 128, swing arm 126 and light emitting member 120 in the varus/valgus orientation. This movement adjusts the direction of plane of light 122 such that, as shown in FIG. 2C, light 122 may be directed approximately along a midline of the anterior surface of the tibia T. Positioning device 110 is configured such that when plane of light 122 is directed along approximately the midline of the anterior surface of the tibia T, as in FIG. 2C, cutting guide 112 is oriented in a desirable varus/valgus orientation for making a tibial bone cut.

Figure 2D:
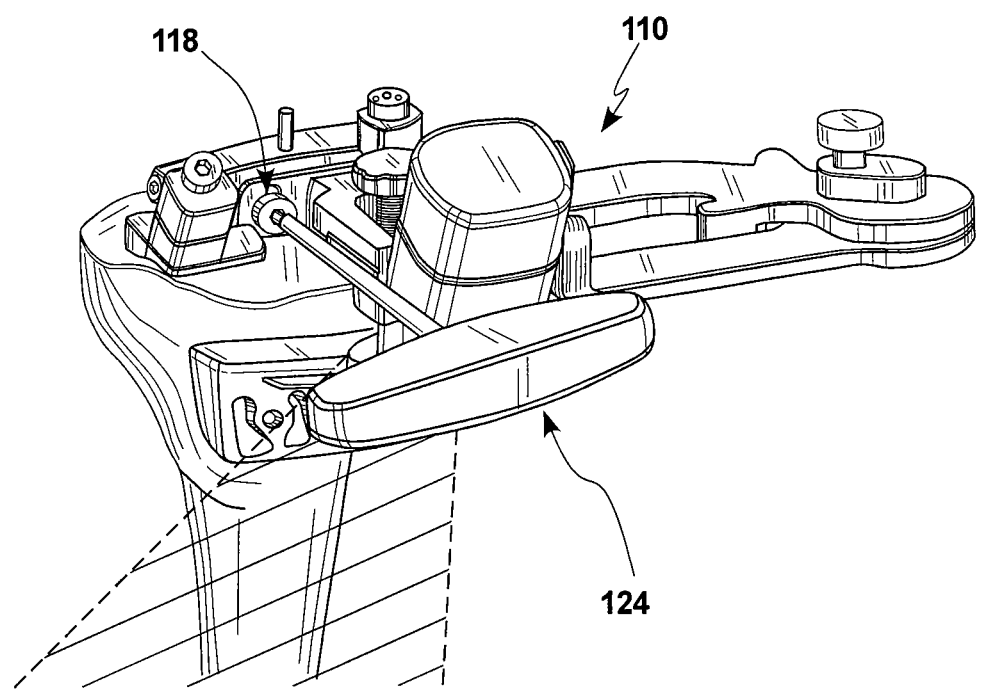

In one embodiment, and with reference now to FIG. 2D, adjustment device 124 may next be used to lock in the varus/valgus adjustment of positioning device 110 via locking member 118. In alternative embodiments, it may not be necessary to lock in the varus/valgus adjustment or the adjustment may be locked in automatically by an automatic locking mechanism of device 110.

Figure 2E:
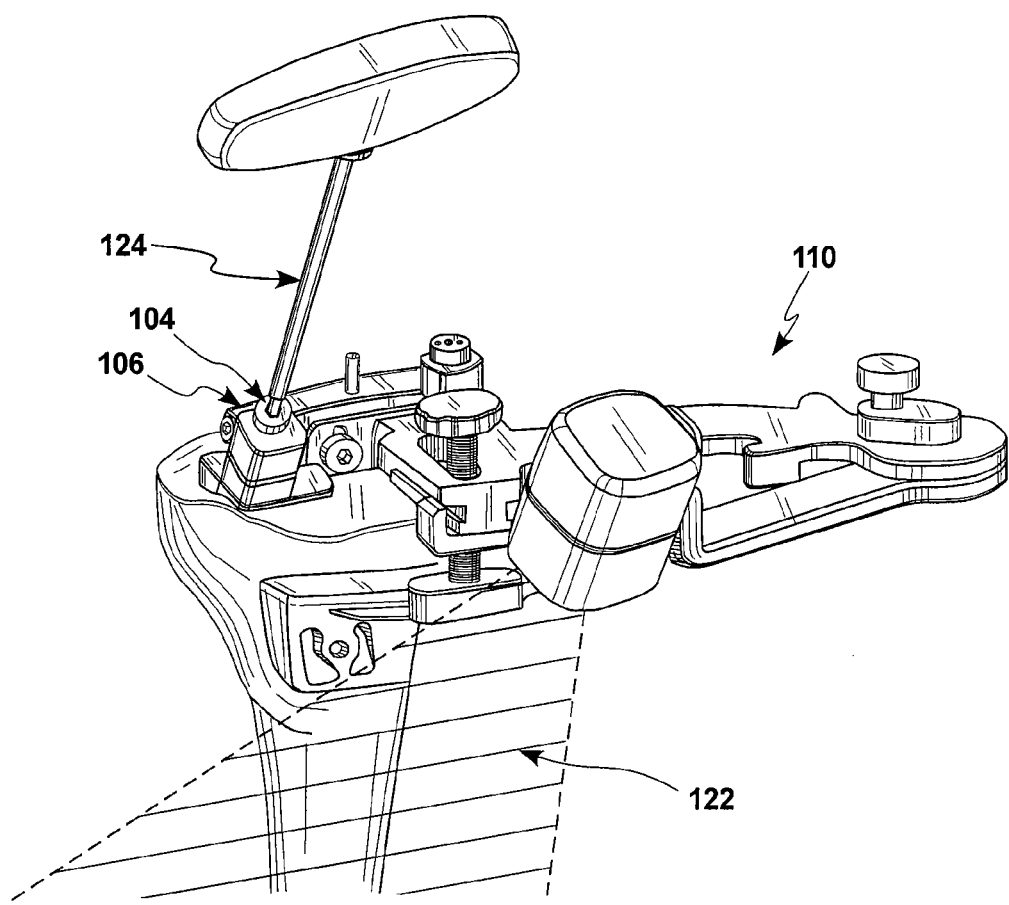
Figure 2F:
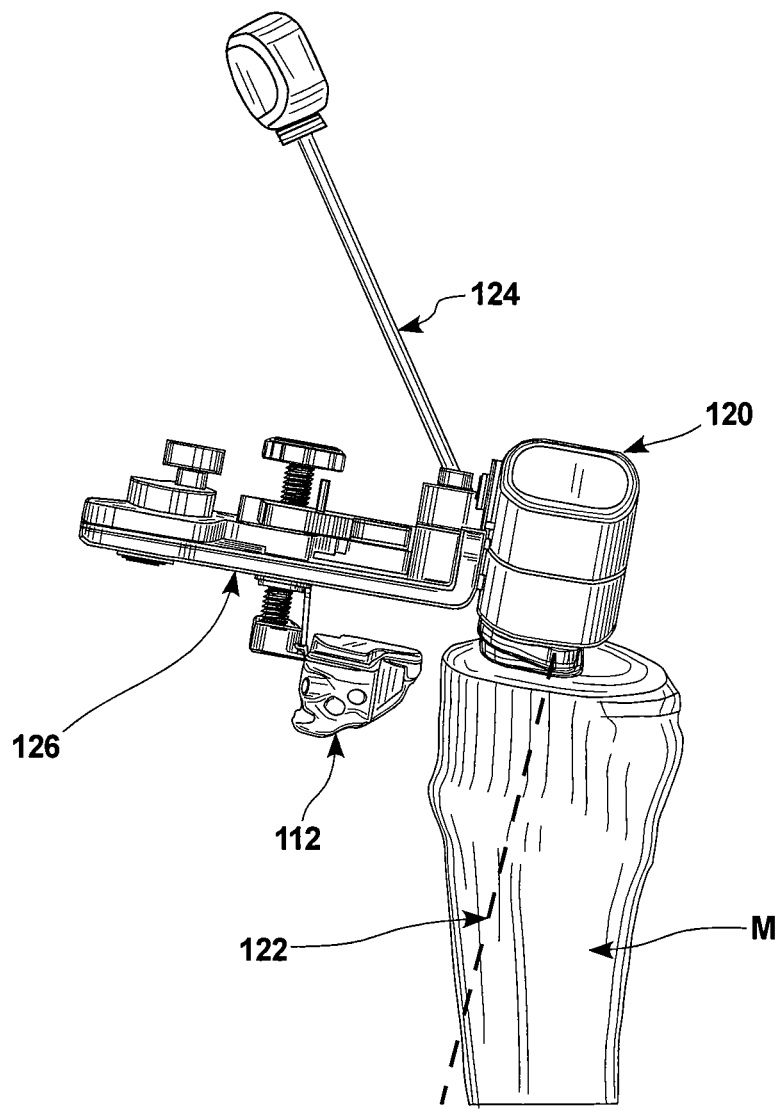

Referring to FIG. 2E, adjustment device 124 may next be coupled with anterior/posterior adjustment member 104. As shown in FIG. 2F, swing arm 126 may be rotated about axle 129 (now visible) approximately 90° to position light illuminating member 120 to direct plane of light 122 along the medial side M of the tibia T. Although in an alternative embodiment the lateral side L of the tibia T may be used for the bone cut positioning method, the medial side M is generally the preferred side for orienting and positioning device 110 and cutting guide 112.

Figure 2G:
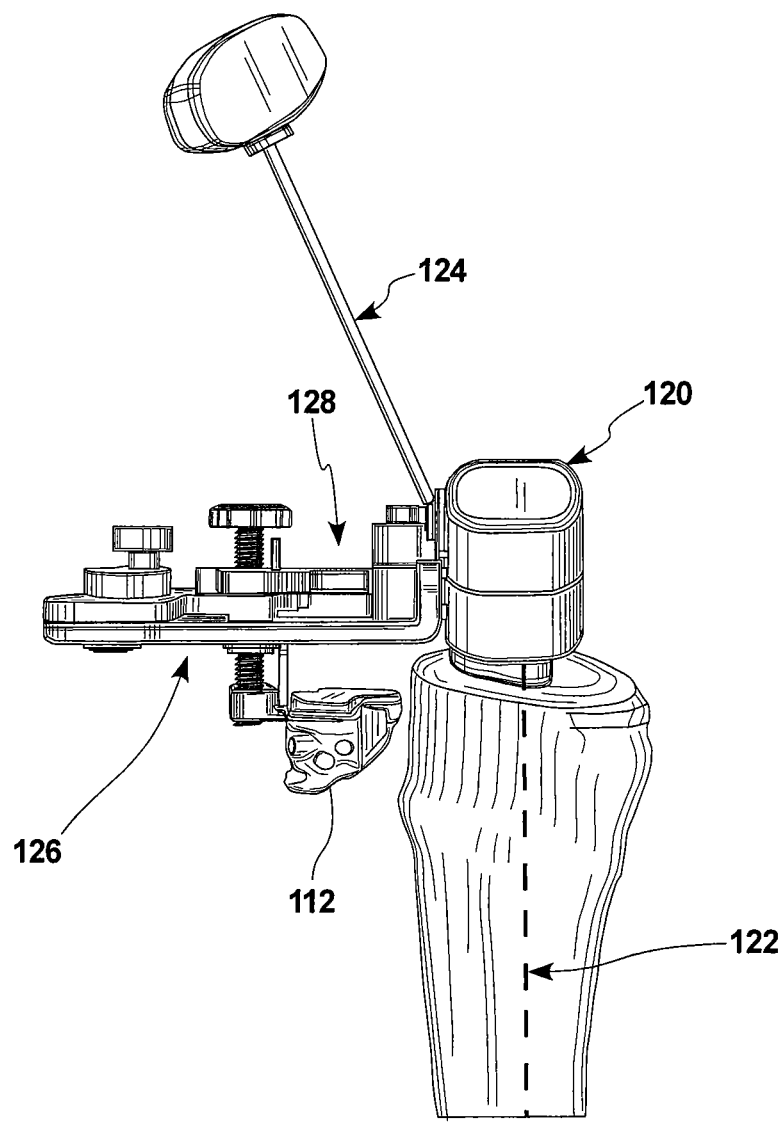

As shown in FIG. 2G, adjustment device 124 may next be used to adjust anterior/posterior adjustment member 104 (not visible) and thus move coupler 106, rotationally moveable arm 128, swing arm 126 and light emitting member 120 to direct plane of light 122 approximately along the midline of the medial side M of the tibia T. As seen when comparing FIGS. 2F and 2G, as positioning device 110 is adjusted, cutting guide's 112 orientation relative to the tibia is also adjusted. In one embodiment, the anterior/posterior orientation may be locked in place via a second locking member. However, this second locking is optional and is not included in the embodiment shown in the figures.

Figure 2H:
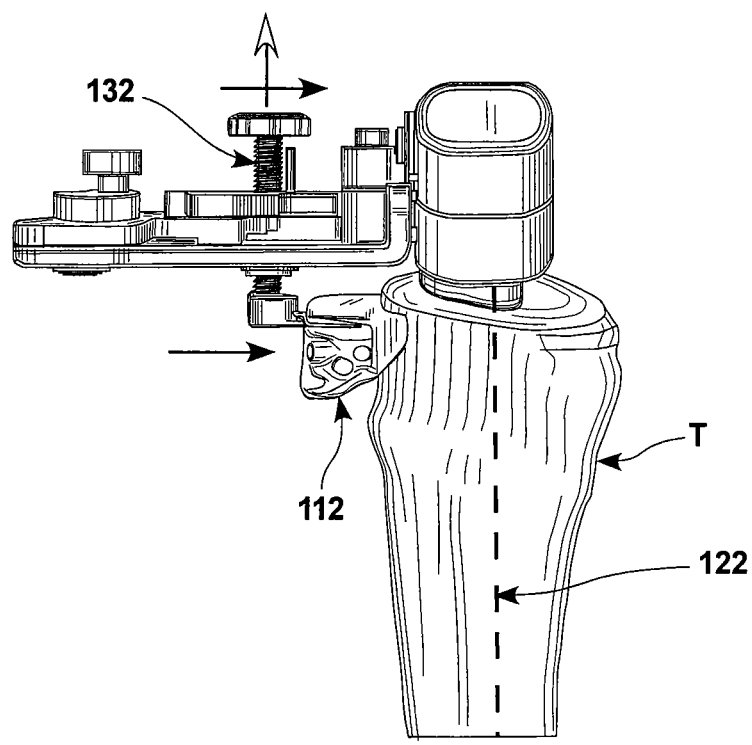

Referring now to FIG. 2H, once varus/valgus and anterior/posterior adjustments have been made, tibial bone resection level adjustment member 132 may turned to move cutting guide 112 up or down relative to the tibia T (hollow-tipped arrow shows upward movement). This upward or downward adjustment may be made by the physician, depending on a desired location of the cutting guide relative to the tibia T. Adjustment member 132 may then be slid along slot 108 (not visible) to move cutting guide 112 into contact with the tibia T (solid-tipped arrows show horizontal movement).

Figure 2I:
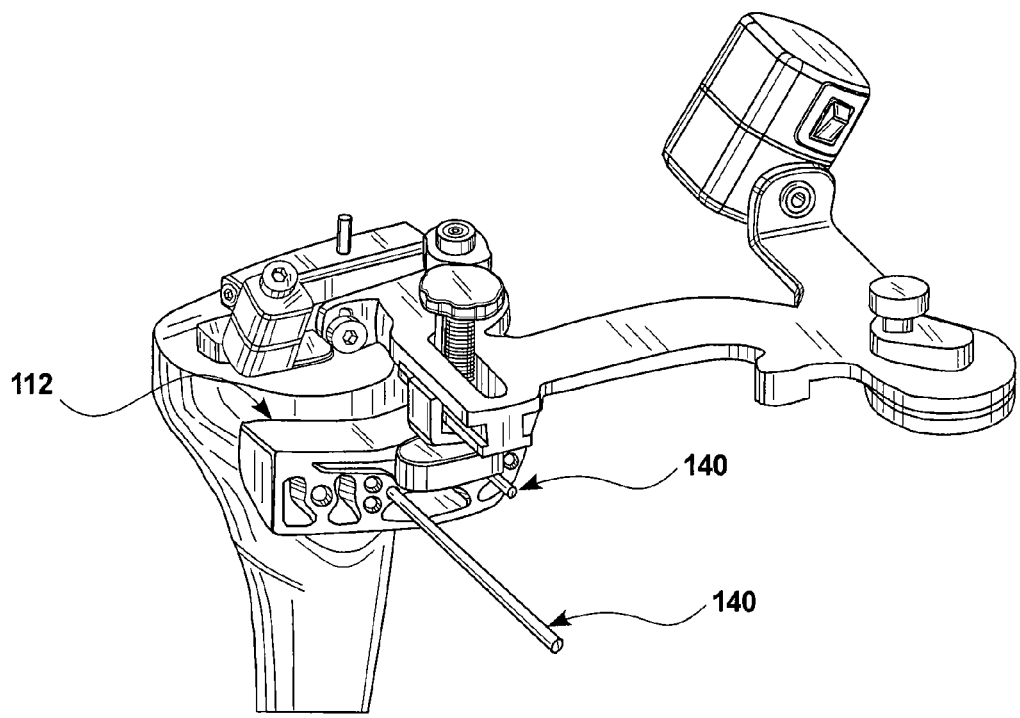
Figure 2J:
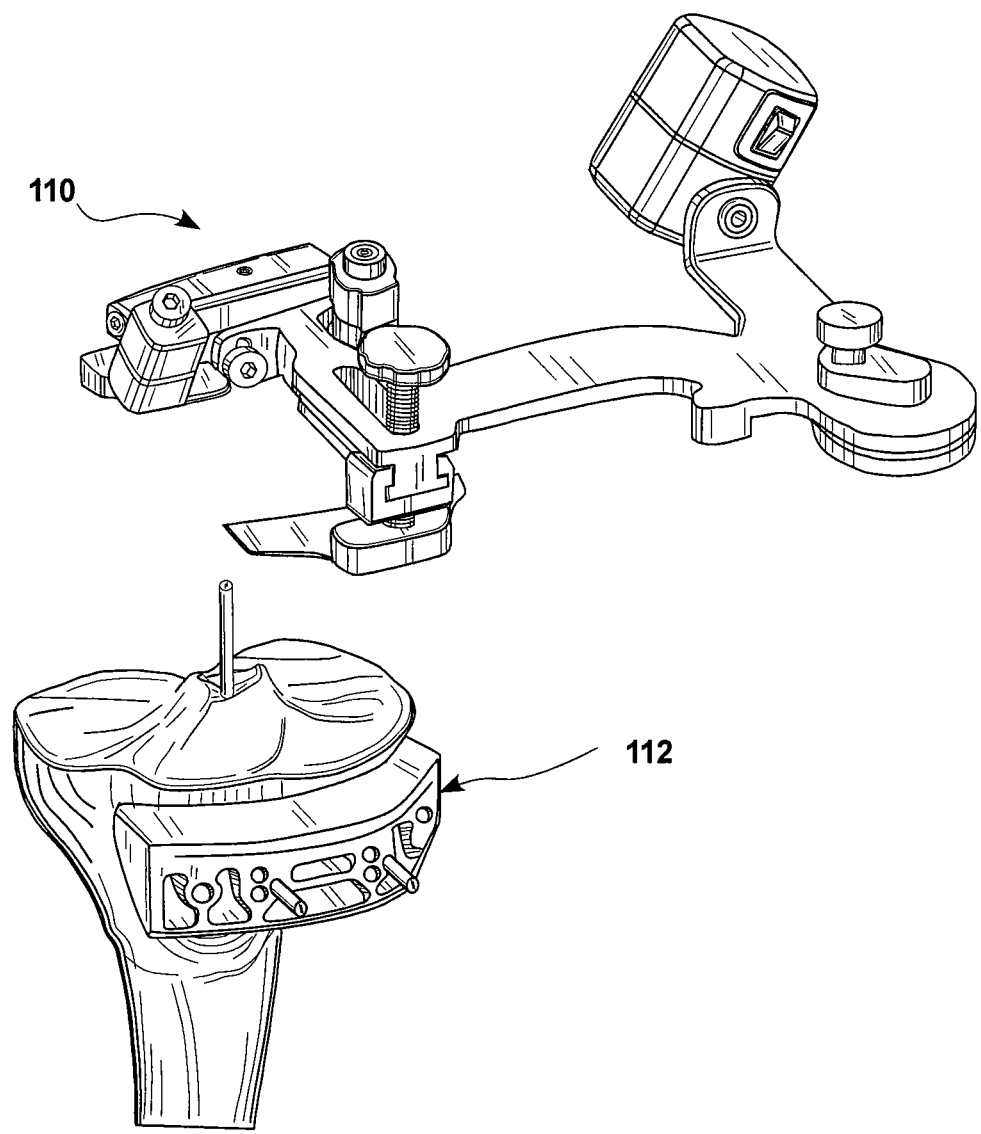

Once cutting guide 112 is in contact with the tibia T, it may be attached to the tibia T using one or more bone attachment pins 140 (or "rods"), as shown in FIG. 2I. Finally, as shown in FIG. 2J, positioning device 110 may be removed, leaving behind cutting guide 112, which the physician may then use to guide a saw blade to cut off a slice of bone from the proximal end of the tibia T. Once the tibial bone cut is made, cutting guide 112 is removed and the rest of the TKA or other knee surgery procedure is performed. As mentioned above, in alternative embodiments, positioning device 110 may be used to mark or otherwise guide a tibial bone cut, thus removing the need for cutting guide 112. In either case, positioning device 110 helps position tibial bone cuts to enhance ligament balancing during a TKA or other knee surgery procedure, and to assure proper alignment of the tibia to the femur.

Figure 3D:
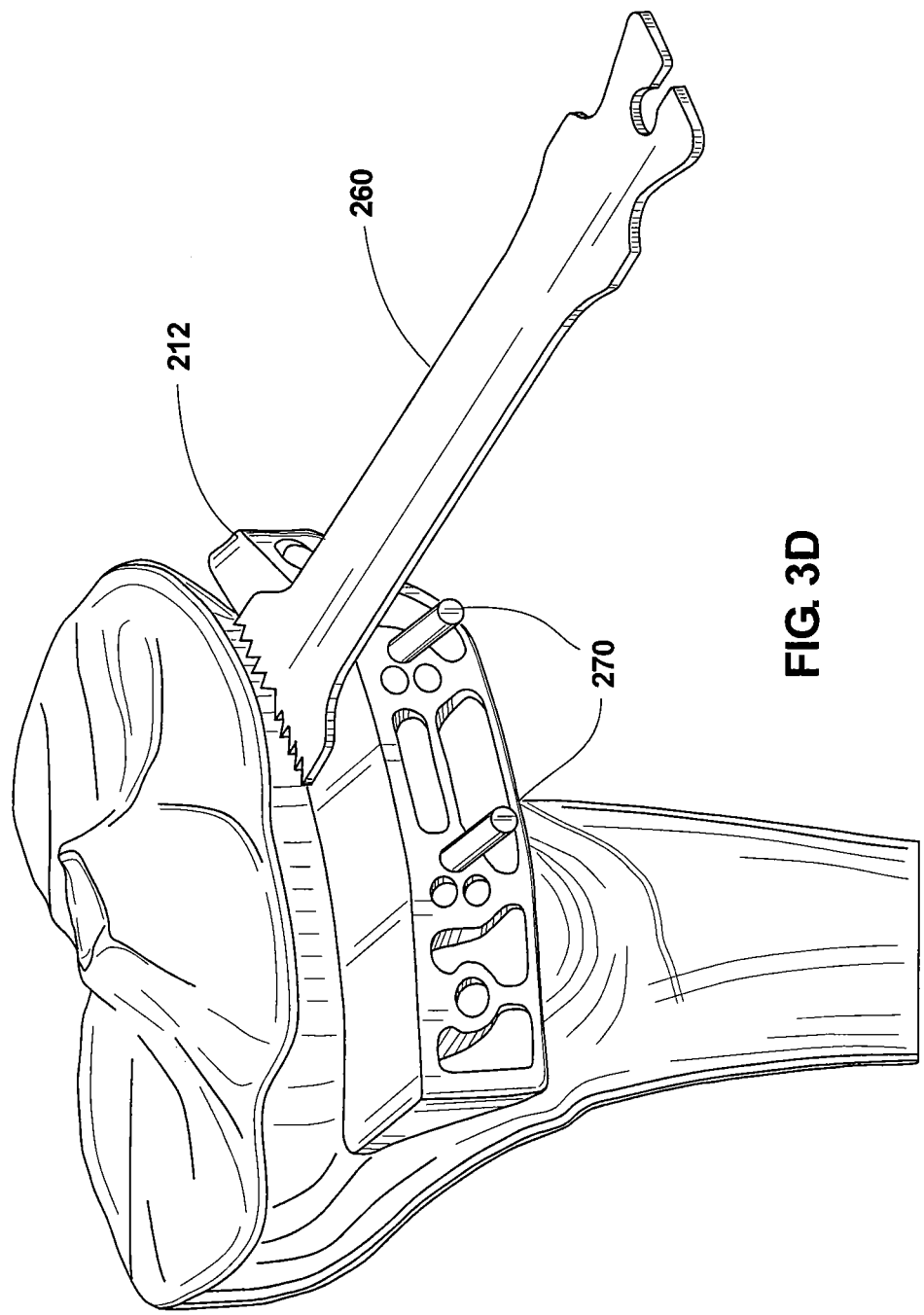
FIG. 3D is a perspective view of a tibia with attached cutting guide and tibial bone saw blade in place after positioning of the cutting guide using the positioning system of FIGS. 3A-3C.
Figure 3A:
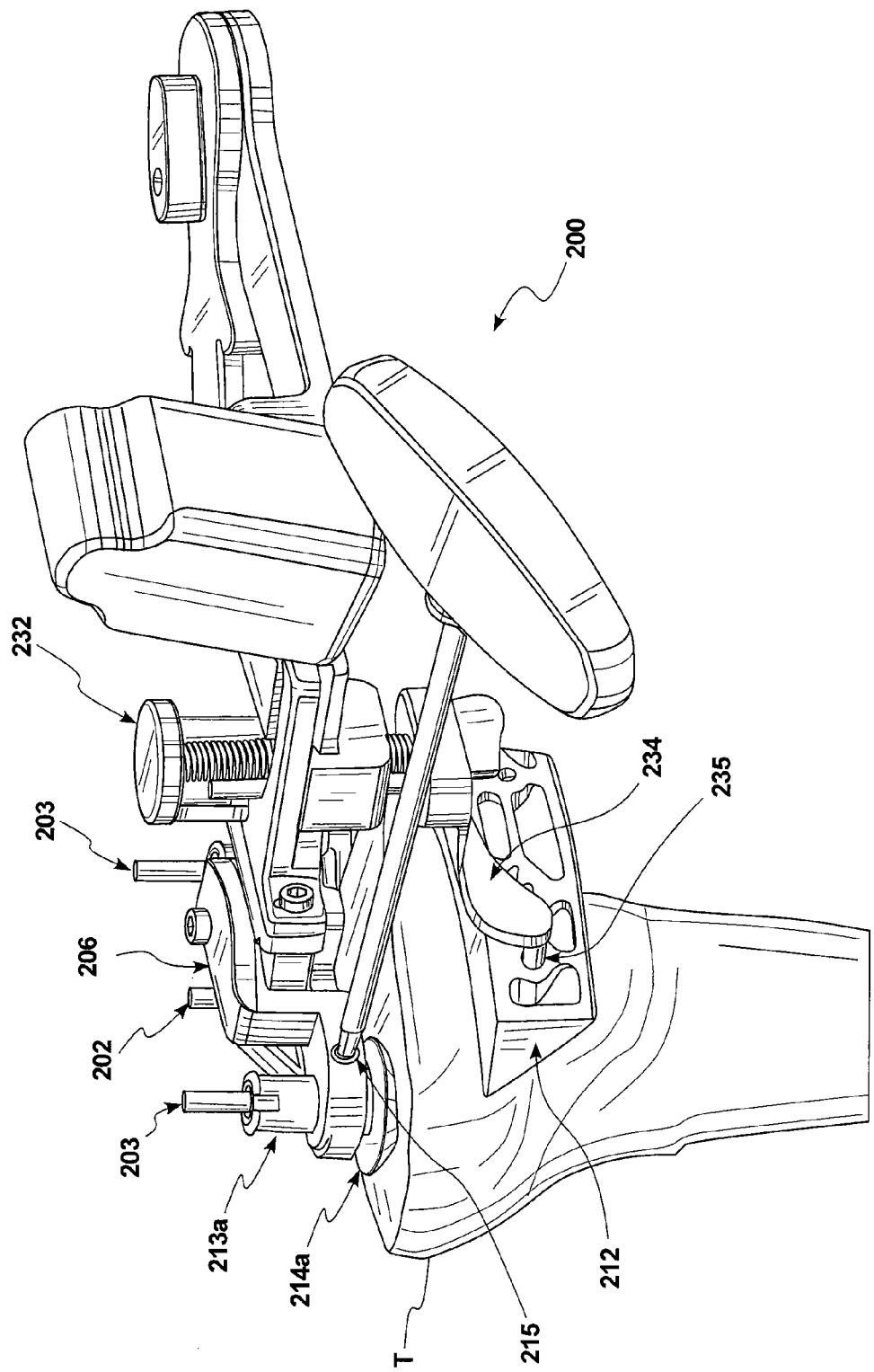
FIG. 3A is a perspective view of a bone cut positioning system coupled with a proximal end of a tibia, according to an alternative embodiment.
Figure 3B:
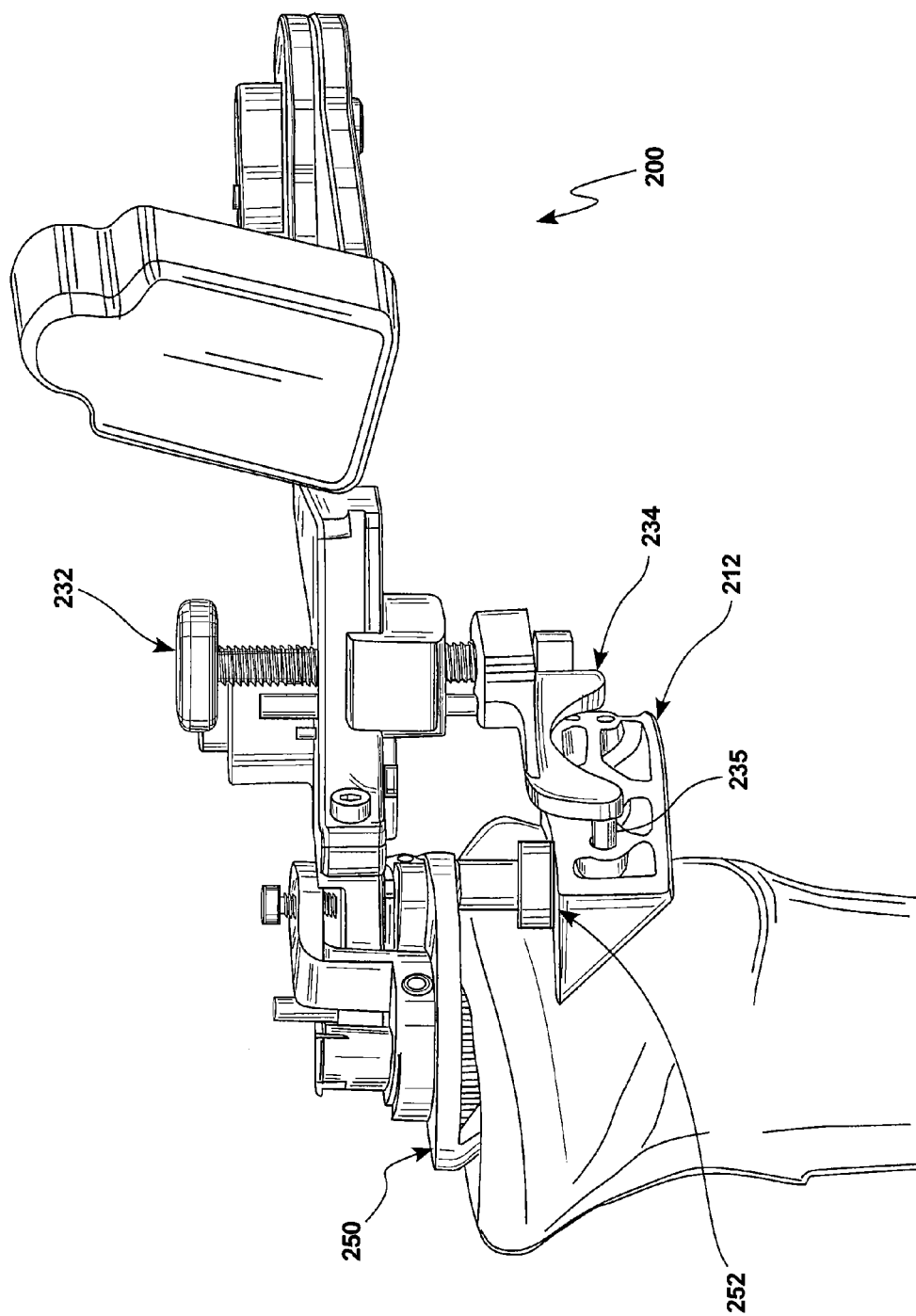
FIGS. 3B and 3C are perspective and posterior views, respectively, of the positioning system of FIG. 3A with the addition of an optional stylet.
Figure 3C:
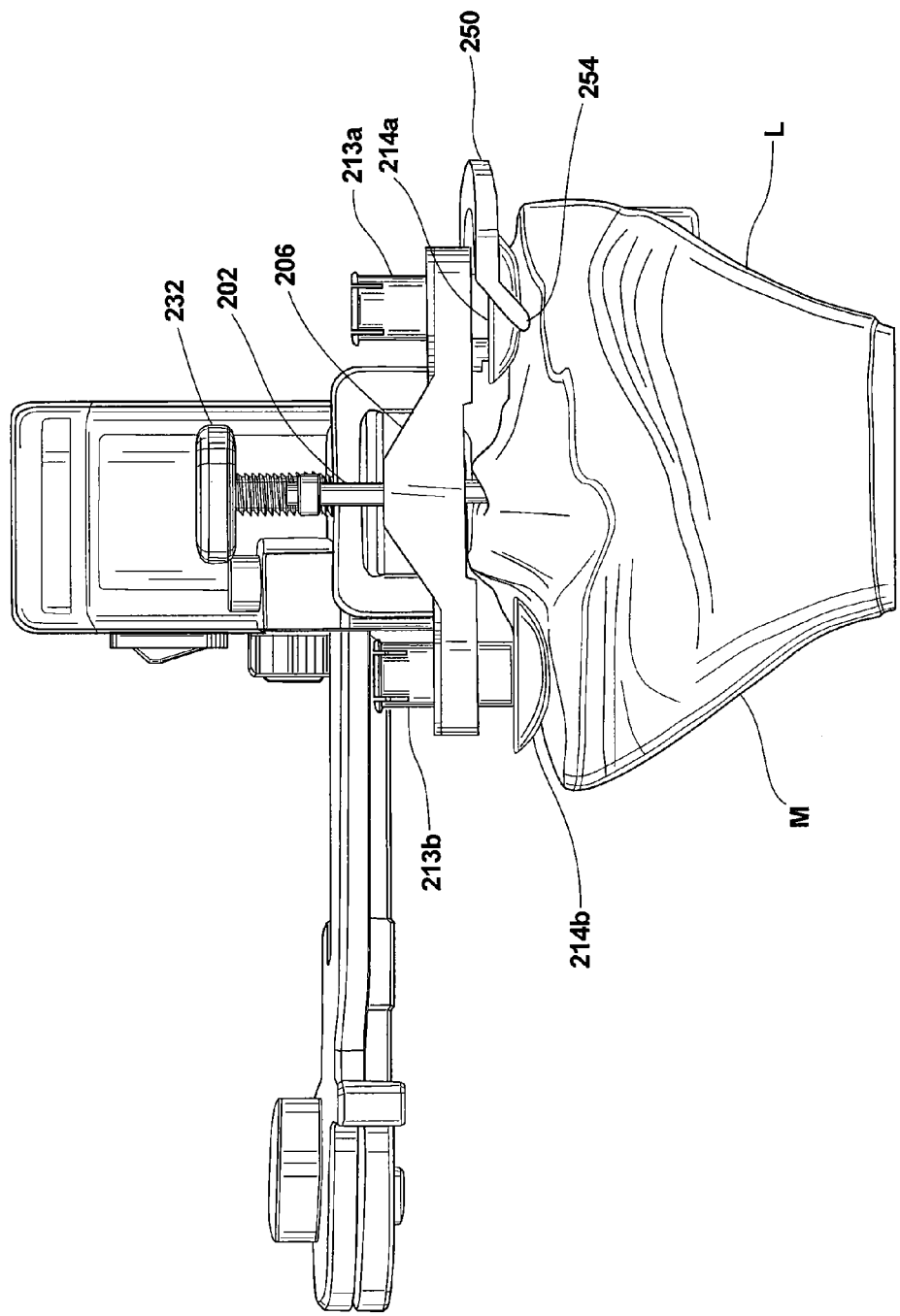

Referring now to FIGS. 3A-3C, another embodiment of a system 200 for positioning a tibial bone cut is shown. Many of the features of system 200 are the same or similar to those described above in reference to FIGS. 1A-1D, and thus those features will not be described here again. In this embodiment, as best seen the posterior view of FIG. 3C, a tibial attachment member 213 includes a lateral attachment member 213a with a lateral footpad 214b and a medial attachment member 213b with a medial footpad 214b. Attachment members 213a, 213b are attached to a tibia T via two reference pins 203, and a coupler 206 is attached to attachment members 213a, 213b. As shown in FIG. 3A, in some embodiments, attachment members 213a, 213b may be locked to coupler 206 using a lock screw 215 or other locking mechanism. As also shown in FIGS. 3A and 3C, coupler may in some embodiments also be attached to the tibia T via another reference pin 202.

System 200 includes an alternative cutting guide holder 234, which includes two rods 235 on which cutting guide 212 rests during adjustments of system 200 to select a desired location for cutting guide 212. As in the previously described embodiment, holder 234 is attached to a bone cut resection level adjustment member 232 configured to move holder 234 up and/or down to select a desired resection level. Adjustment member 232 can also move back and forth through a slot on the rotationally moveable arm, as previously described, to bring cutting guide 212 into or out of contact with the tibia T.

With reference to FIGS. 3B and 3C, in some embodiments, system 200 may include a stylus 250 for determining a bone cut resection level. Stylus 250 is coupled with tibial attachment member 213 and/or coupler 206, according to various embodiments. As seen in FIG. 3C, stylus 250 contacts one of the articular surfaces of the tibia via a tibial contact 254. In the embodiment shown, the lateral articular surface is contacted. As seen in FIG. 3B, stylus 250 wraps around the tibia T and extends to a resection level bumper 252, against which cutting guide 212 may be adjusted to select a desired bone resection level. In this embodiment, wherein tibial contact 254 contacts the lateral articular surface of the tibia T, the contact point of bumper 252 may be between about 8 mm and about 11 mm below the lateral articular surface, and in some embodiments between about 9 mm and about 10 mm below the lateral articular surface. If stylus 250 is instead coupled with a medial articular surface, bumper 252 will likely extend to a different level below the medial articular surface. Generally, stylus 250 is used to help select a desired tibial resection level at which to place cutting guide 212 by adjusting adjustment member 232.

Referring now to FIG. 3D, tibial cutting guide 212 is shown attached to the tibia T via two attachment rods 270 (or "pins"). In alternative embodiments, only one rod 270, more than two rods 270, or any suitable alternative fasteners may be used to attach cutting guide 212 to the tibia T. After cutting guide 212 is attached, a tibial bone saw blade 260 is then used to make the bone cut (or multiple cuts) on the proximal tibia T. Blade 260 is attached to a bone saw (not shown) to make the cut.

Once the tibial bone cut is made, cutting guide 212 is removed and the remainder of the TKA or other knee arthroplasty procedure is performed.

Figure 4F:
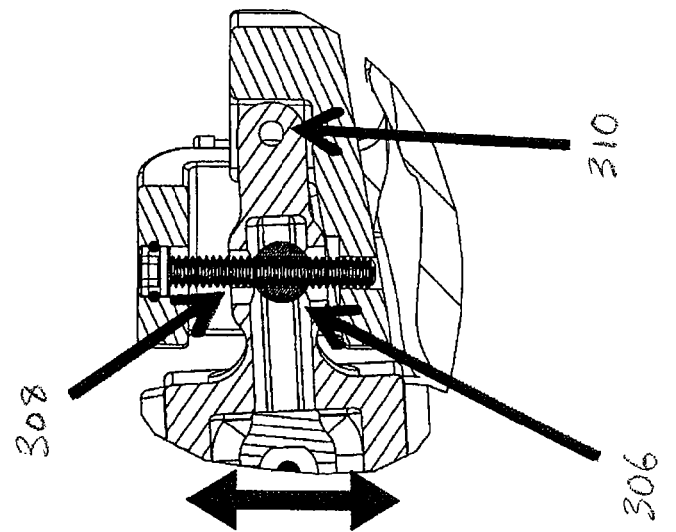

Referring now to FIGS. 4A-4H, a tibial attachment member 300 of a tibial bone cut positioning system according to one embodiment is shown. In this embodiment, as shown in FIG. 4A, tibial attachment member 300 includes three fixation holes 302, which are offset relative to one another to provide enhanced stability to attachment member 300 when attached to a tibia. Tibial attachment member 300 may further include two tibial contact feet 304 (FIG. 4C) for contacting medial and lateral articular surfaces of the tibia. These contact feet 304 may be independently movable and/or lockable in some embodiments. Feet 304 may also be designed to slip under the femur and provide consistent contact with the tibia, as shown in FIG. 4B.

Figure 4E:
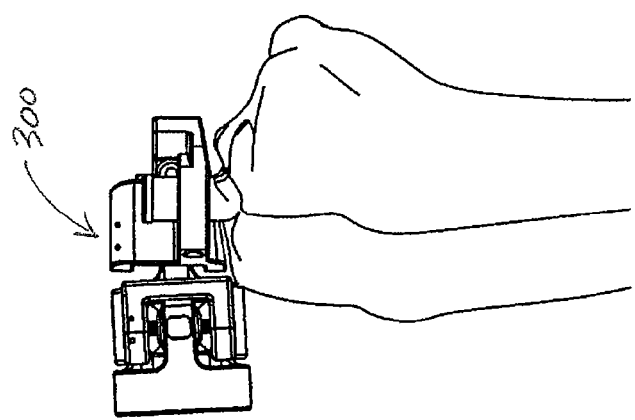
Figure 4D:
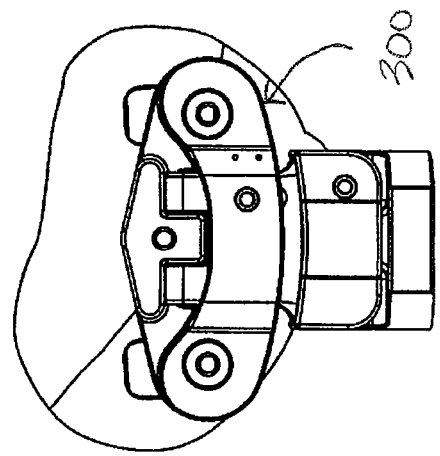

FIGS. 4D-4F are top, side and cross-sectional views, respectively, of tibial attachment member 300, showing tibial slope (or "anterior/posterior") adjustment apparatus 306, 308, 310. In the cross-sectional view of FIG. 4F, adjustment apparatus can be seen to include a captured ball 306, a captured screw 308 and a pivot 310. In this embodiment, captured screw 308 may be adjusted relative to captured ball 306 to move tibial attachment member 300 about pivot 310 and thus adjust the tibial slope (or "anterior/posterior orientation") of tibial attachment member 300. In alternative embodiments, other adjustment mechanisms may be used, and thus this embodiment is provided as an example only.

Figure 4I:
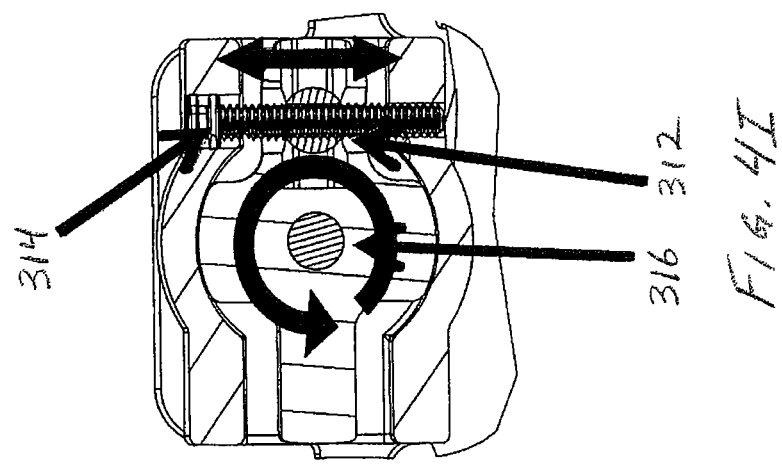
Figure 4H:
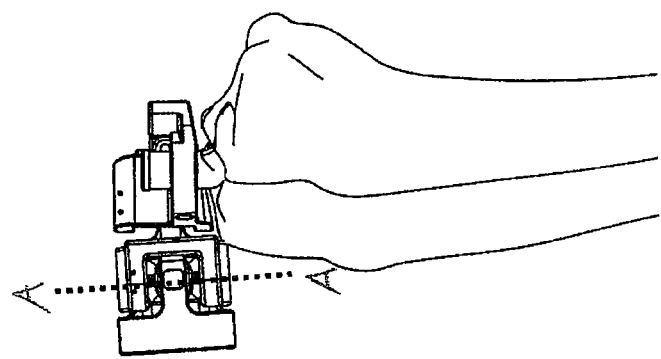
Figure 4G:
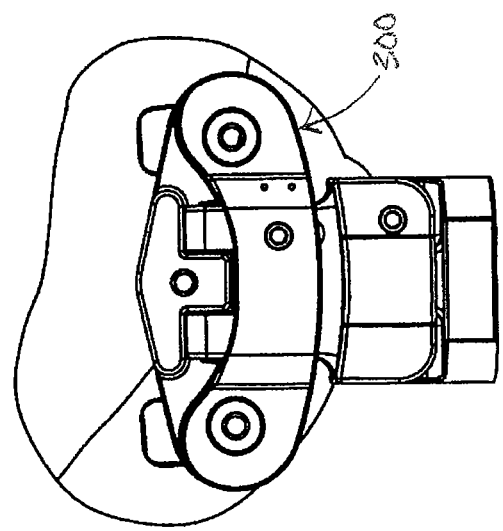

FIGS. 4G-4I are top, side and cross-sectional view, respectively, of tibial attachment member 300, showing varus/valgus (or "medial/lateral") adjustment apparatus 312, 314, 316. In the cross-sectional view of FIG. 4I, taken through dotted line A-A in FIG. 4H, adjustment apparatus can be seen to include a captured ball 312, a captured screw 314 and a pivot 316, similar to the adjustment apparatus for tibial slope. Again, captured screw 314 may be adjusted relative to captured ball 312 to move tibial attachment member 300 about pivot 316 and thus adjust the varus/valgus (or "anterior/posterior") orientation of tibial attachment member 300. Again, in alternative embodiments, other adjustment mechanisms may be used.

Figure 5A:
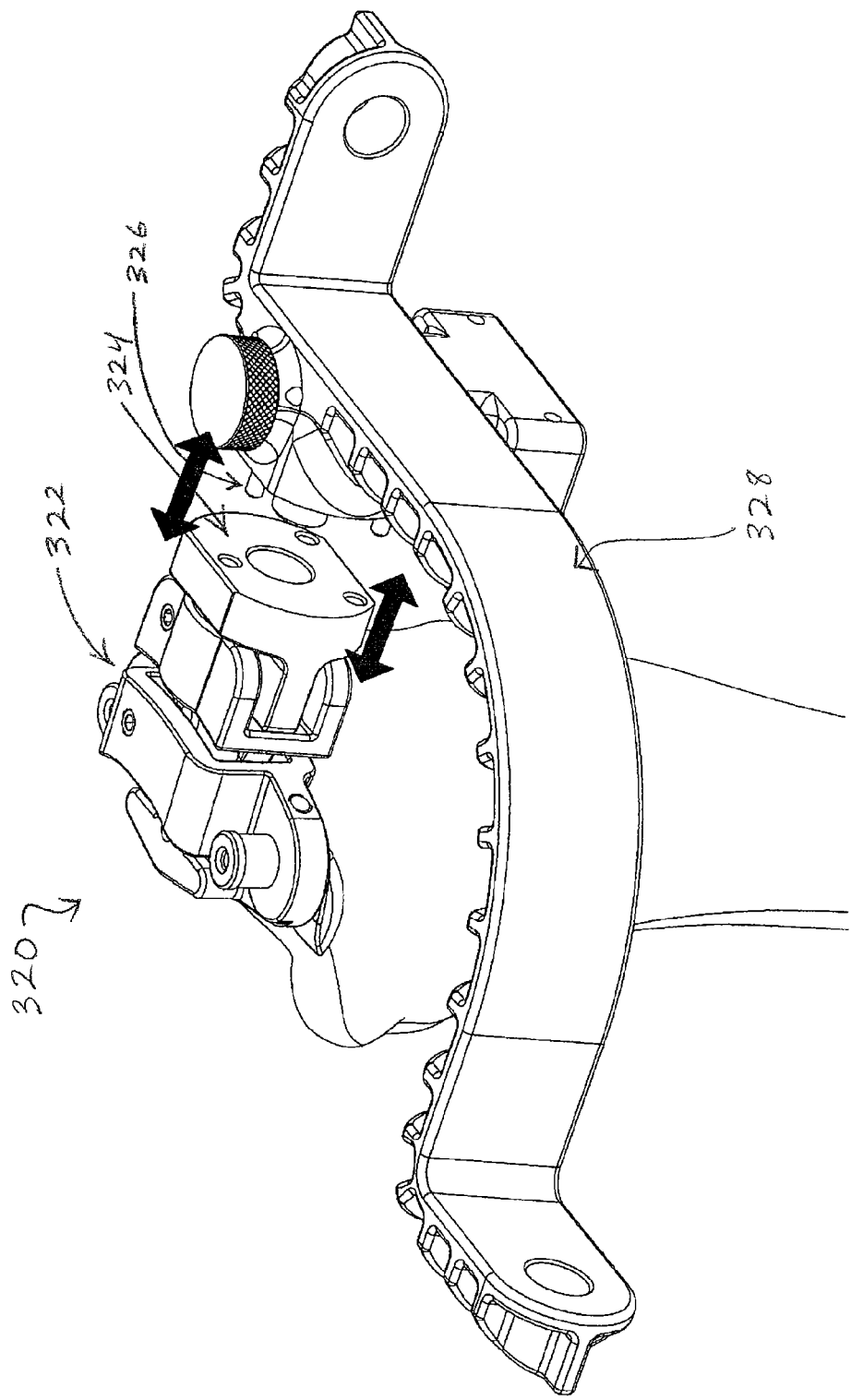

Referring now to FIGS. 5A-5I, an alternative embodiment of a tibial bone cut positioning system 320 is shown in various views. As shown in FIG. 5A, in one embodiment, bone cut positioning system 320 may include a tibial attachment member 322 removably couplable with an arm 328. Attachment member 322 and arm 328 may be coupled with one another via any acceptable means in various embodiments. For example, in the embodiment shown, attachment member 322 may include a magnetic attachment plate 324 that mates with a magnetic attachment plate on arm 328. Pins 326 on the magnetic attachment plate of arm 328 may fit into holes on the magnetic attachment plate 324 of attachment member 322. This configuration may facilitate removal and attachment of arm 328 to attachment member 322, thus making the overall system 320 less cumbersome and easier to use.

Turning now to FIG. 5B, arm 328 generally includes a first attachment point 330a and a second attachment point 330b for removably attaching a laser light emitter 340 (FIG. 5C) to arm 328. As shown, arm 328 generally extends approximately 90 degrees about an arc, although arm 328 itself need not be shaped as an arc. Attachment points 330a, 330b are located at or near opposite ends of arm 328, so that when arm 328 is attached to tibial attachment member 322, attachment points 330a, 330b are generally positioned so that an attached laser light emitter 340 will address anterior and side aspects of a tibia (either medial or lateral). Attachment points 330a, 330b may attach with laser light emitter 340 via magnetic force attachment, similar to the attachment of arm 328 to tibial attachment member 322. In one embodiment, each end of arm 328 may include one attachment point 330a, 330b (or "magnetic contact area"), as shown in FIG. 5B. Alternatively, as shown in FIG. 5I, another embodiment of an arm 322 may include attachment points 334 (or "magnetic contact areas") at each end of arm 322. Alternatively, as shown in FIG. 5J, another embodiment may include magnetic attachment points to a rotational swing arm 126. In yet other embodiments, light emitter 340 may attach to arm 328 via any other suitable attachment means.

Figure 5F:
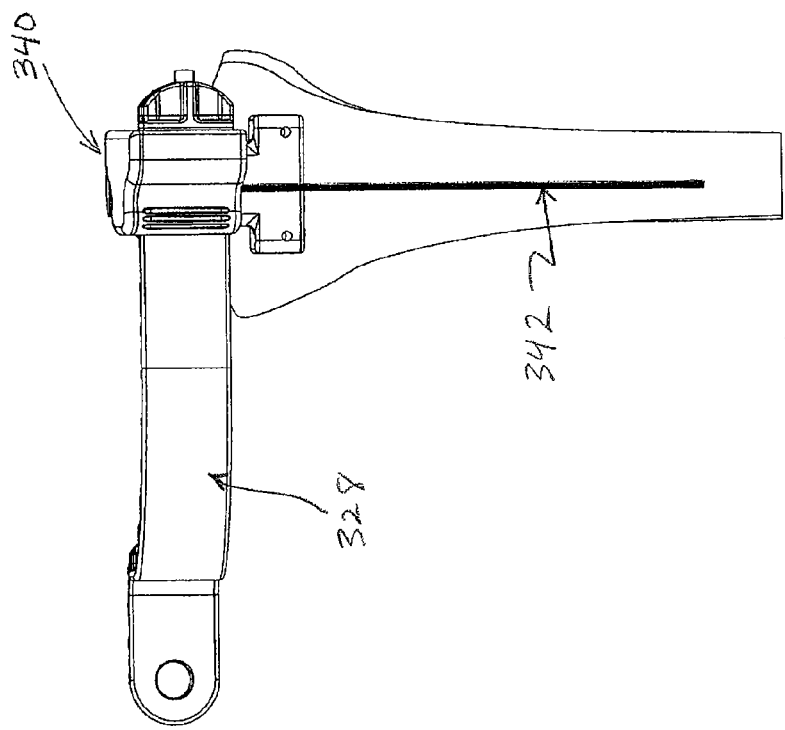
Figure 5E:
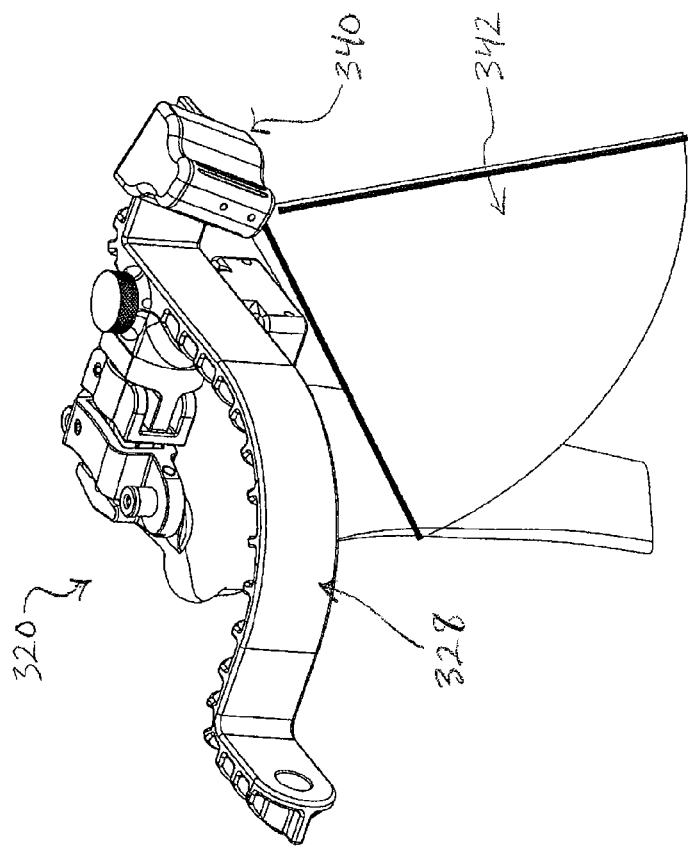
Figure 5H:
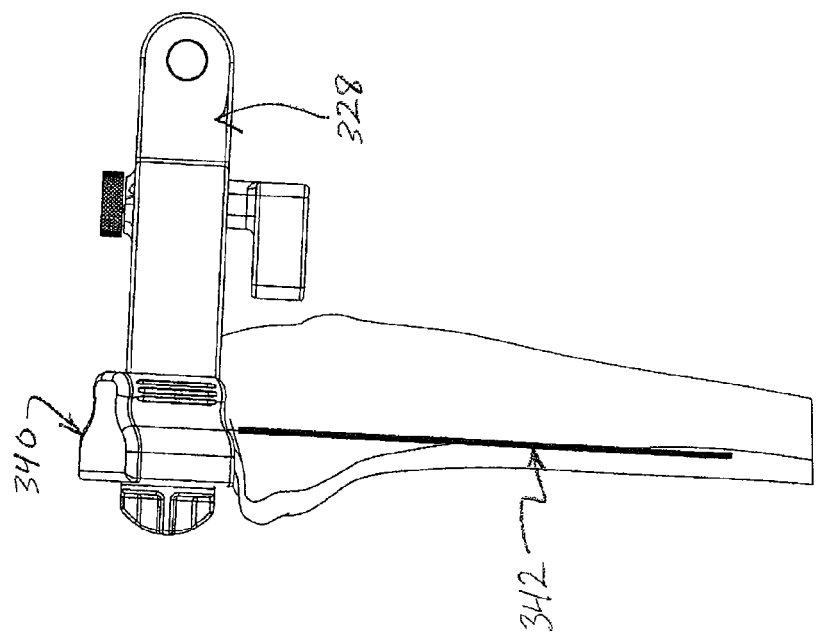
Figure 5G:
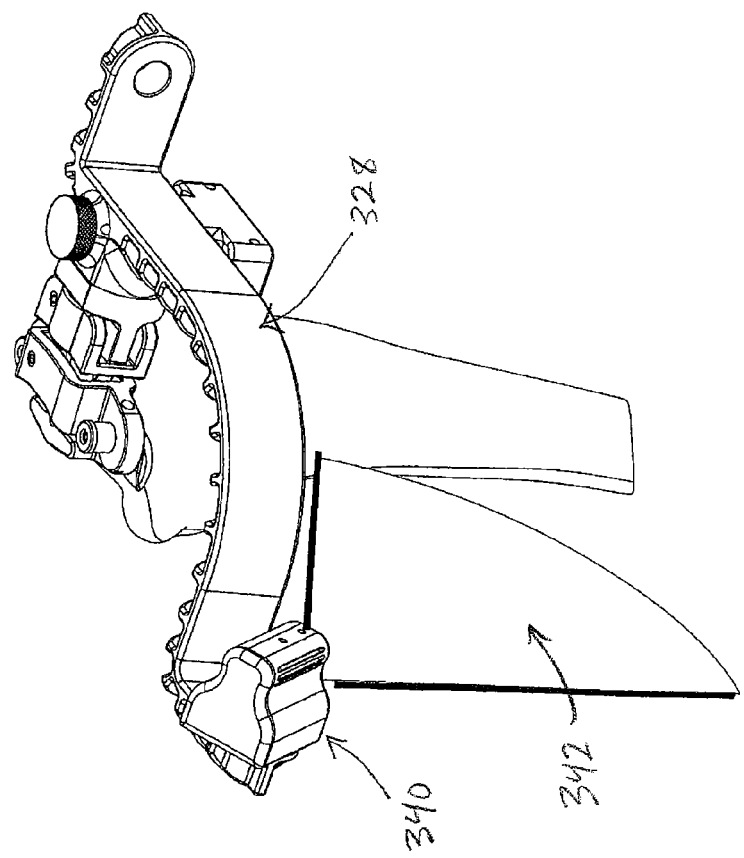

FIGS. 5D-5H show laser light emitter 340 attached at various points to arm and emitting light 342 toward a tibia from various angles. In one embodiment, light emitter 340 may not be turned on until it is attached to arm 328 via its magnetic attachment (or other attachment means). This control make act as a safety mechanism to prevent light emitter 340 from being turned on prematurely or from being left on accidentally after use. In one embodiment, light emitter 340 may turn on automatically when attached to arm 328 and turned off automatically when removed from arm 328. The simple removability and attachment of light emitter 340 relative to arm 328 allows for easy movement from tibial slope adjustment to varus/valgus adjustment and vice versa. FIGS. 5E and 5F show varus/valgus alignment positions, and FIGS. 5G and 5H show tibial slope alignment positions.

Figure 7:
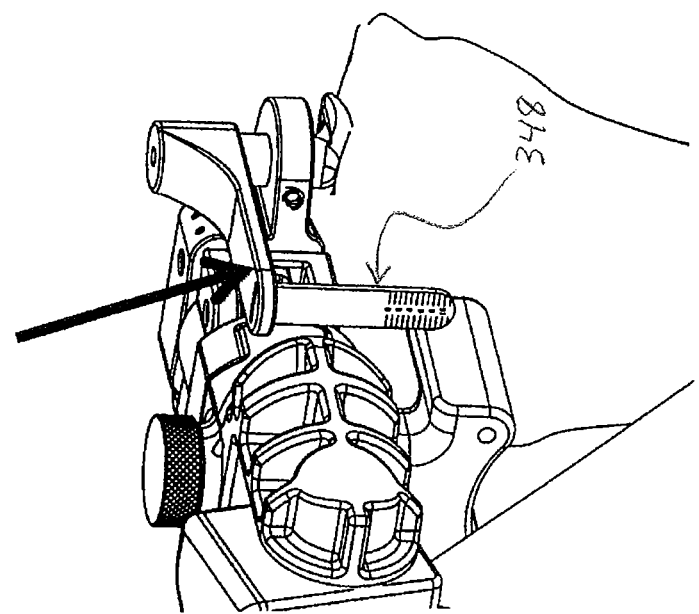
FIG. 7 is a perspective view of a depth guide of one embodiment of a bone cut positioning system.
Figure 6:
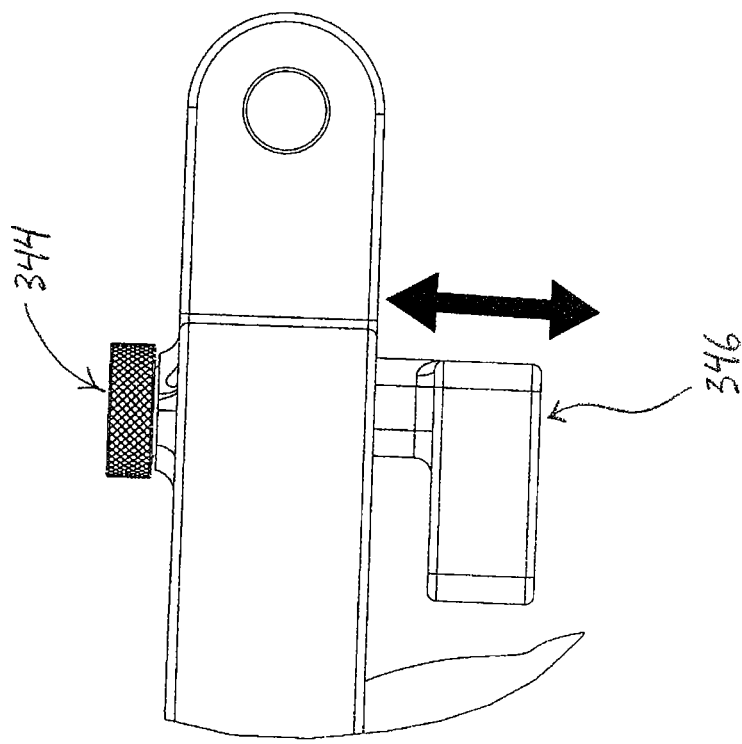
FIG. 6 is a side view of a tibial pin positioning adjustment member according to one embodiment.

Turning now to FIG. 6, in one embodiment a bone resection level adjustment member of a bone cut positioning system may include an adjustment knob 344 coupled with a pin template 346 (or "pin guiding member"). Each turn of knob 344 may drop or raise pin template 346 by a known distance, such as 1 mm in one embodiment. As shown in FIG. 7, some embodiments may further include a depth gauge 348, which may reference off of the trough of the medial or lateral compartment of the tibia for helping a user determine a depth of the bone cut to be made.

Figure 8D:
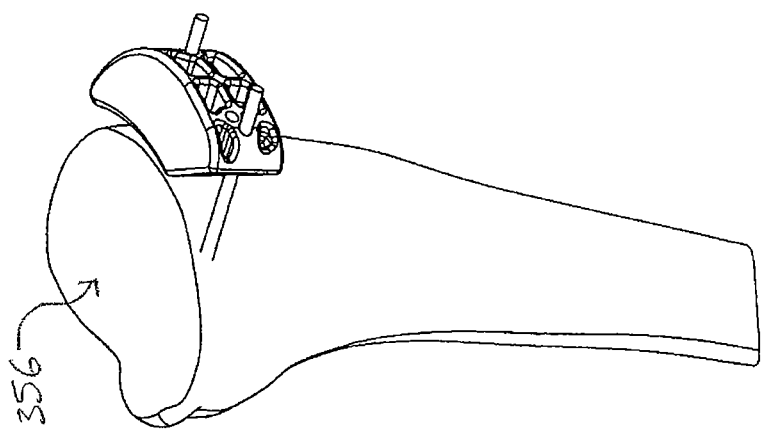
Figure 8C:
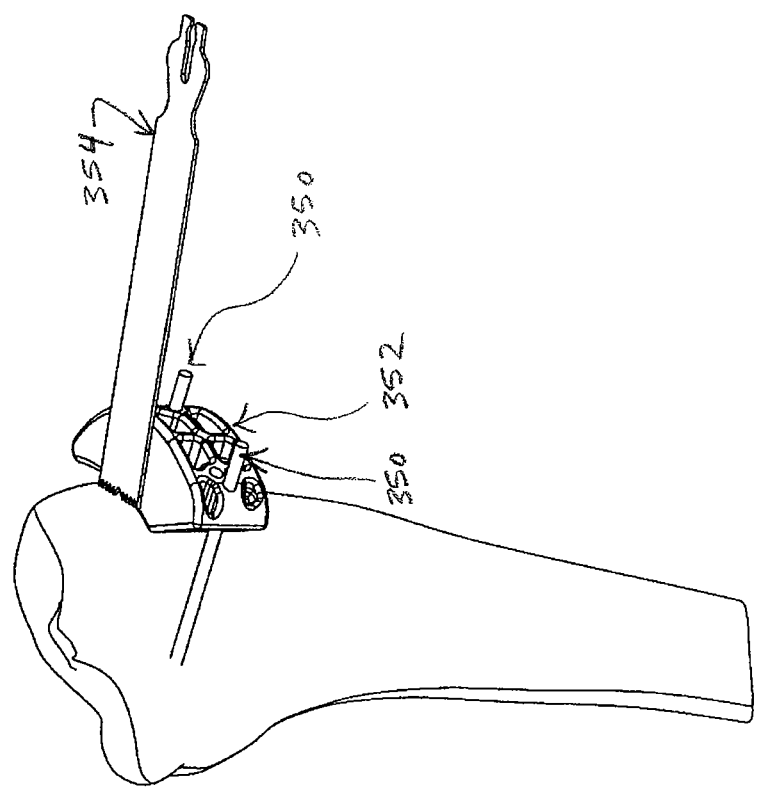

FIGS. 8A-8D demonstrate a method according to one embodiment for making a bone cut on a tibia using a bone cut positioning system 320. As shown in FIG. 8A, once tibial slope, varus/valgus and bone cut level adjustments have been made via system 320, pins 350 may be inserted through holes on pin template 346 and drilled into the tibia. As shown in FIG. 8B, arm 328 and the components of system 320 attached to arm 328 may be removed from tibial attachment member 322. As shown in FIGS. 8C and 8D, a bone cutting guide 352 may then be advanced over pins 350, and a bone saw 354 may be used to make the tibial bone cut.

Referring now to FIGS. 9A-9D, one optional feature of a bone cut positioning system may be a tibial cut check device 360. In use, cut check device 360 is attached to the cut surface of the tibia, either via pins 350 or by holding manually by a user. Visualization features 362 of cut check device 360 may then be used to assess the tibial cut. As shown in FIG. 9B, cut check device 360 may include an attachment plate 364 so that it can be attached to arm 328 using the same attachment means as tibial attachment device 322. As shown in FIGS. 9C and 9D, laser light emitter 340 can then be used with cut check device 360 coupled with arm 328 to check tibial slope and varus/valgus alignment. If the desired alignments were not achieved with the initial cut, additional cuts may be made and checked again until the desired result is achieved.

With reference now to FIGS. 10A-10D, another optional feature of a bone cut positioning system may be one or more depth gauges 370 for helping a user select a desired tibial bone resection level. In one embodiment, for example, multiple depth gauges 370 for different bone cut resection levels may be provided. As shown, for example, one embodiment may include a 3 mm gauge 372a, a 9 mm gauge 370b, and a 10 mm gauge 370c, for measuring a bone resection level. In this embodiment, each gauge 370 includes an LED 372 at the desired level of bone resection—i.e., a 3 mm LED 372a, a 9 mm LED 372b, and a 10 mm LED 372c.

Figure 10A:
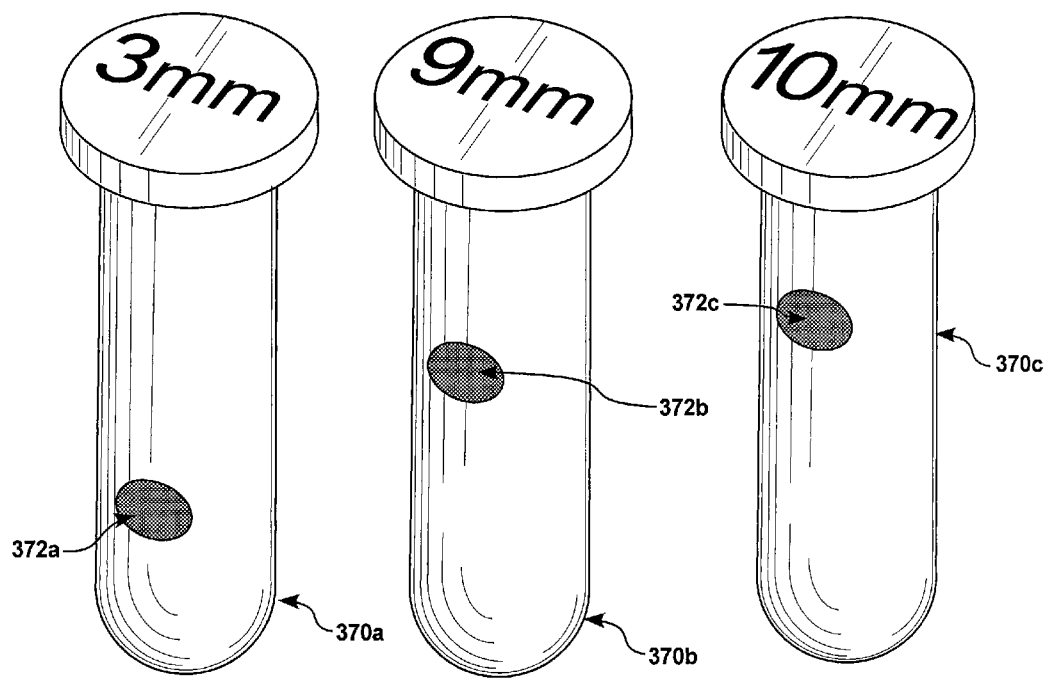
FIGS. 10A-10D show a depth gauge device for a bone cut positioning system according to one embodiment.
Figure 10B:
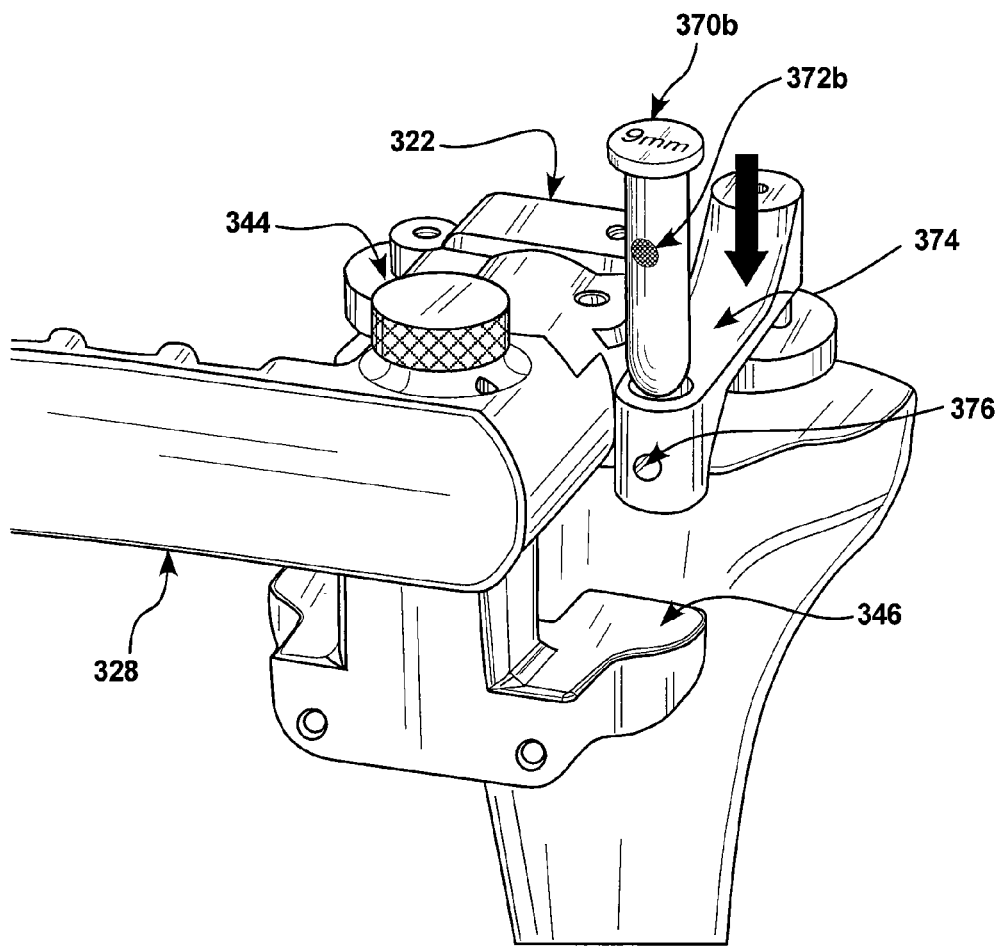
Figure 10C:
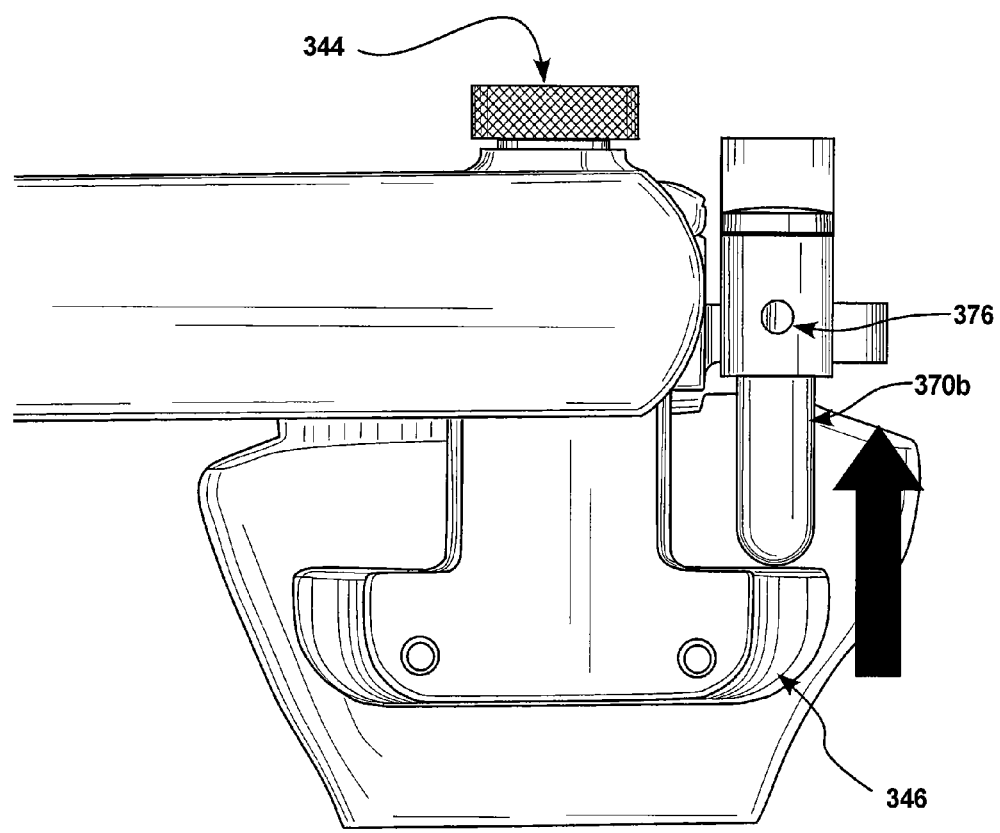
Figure 10D:
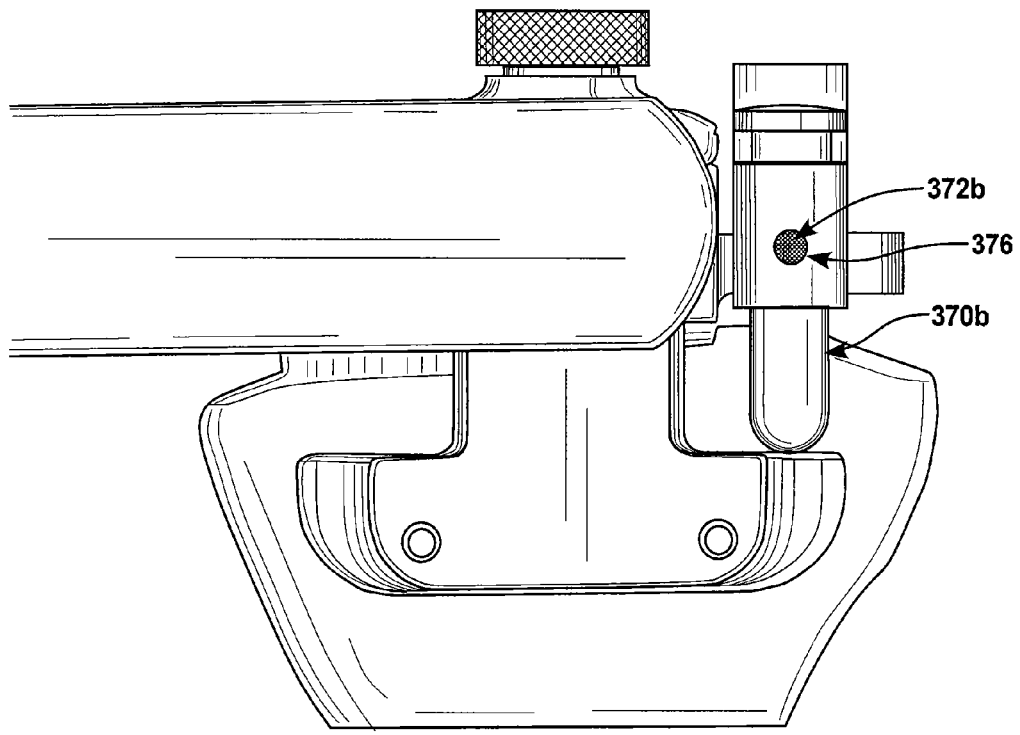

As shown in FIG. 10B, depth gauge 370b may be placed into a depth arm 374, which is attached to tibial attachment member 322 and includes an aperture 376. As discussed previously, a pin template 346 is generally included in the bone cut positioning system and is attached to arm 328 and adjustable via knob 344. As shown in FIG. 10C, turning knob 344 will raise pin template 346 to contact one end of depth gauge 370b. As shown in FIG. 10D, continuing to turn know 344 will continue to raise pin template 346 and thus will push depth gauge 370b upward, so that LED 372b will be visible through aperture 376. At this point, when LED 372b is visible through aperture 376, the user knows the desired depth of bone cut has been reached.

In another embodiment, and with reference now to FIGS. 11A-11E, depth gauges of various heights 380a, 380b, 380c may include colored, reflective or otherwise distinguishable markers 382a, 382b, 382c. Of course, in this or the previous embodiment, any suitable number of depth gauges 380 may be provided, from one to any unlimited number. In some embodiments, multiple depth gauges 380 may be provided as a set or kit, while in other embodiments, depth gauges may be provided individually. Also, although the examples of LEDs 372 are shown in depth gauges 370a, 370b, 370c, and circumferential markers 382 are shown in depth gauges 380a, 380b, 380c, in alternative embodiments any suitable visualization, tactile or other feedback elements may be used to facilitate a user's confirmation that a desired depth has been achieved, such as but not limited to one or more bumps for tactile feedback, colored dots for visualization, or a beeping noise indicating desired depth. Thus, the exemplary embodiments of FIGS. 10A-10D and 11A-11E are provided for exemplary purposes only.

Figure 11A:
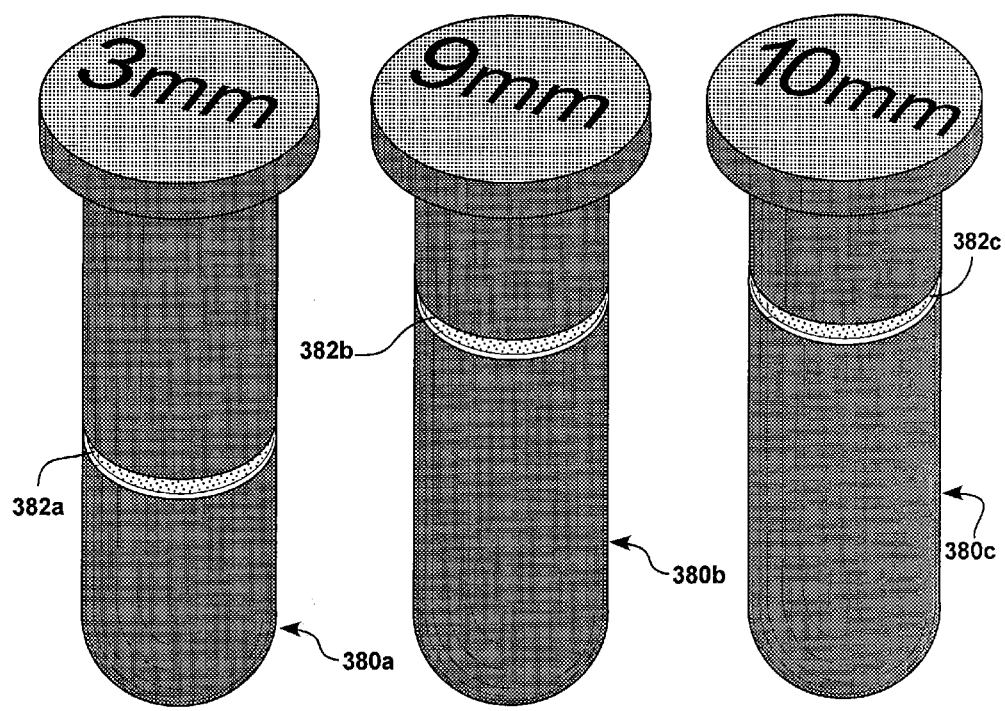
FIGS. 11A-11E show a depth gauge device for a bone cut positioning system according to an alternative embodiment.
Figure 11B:
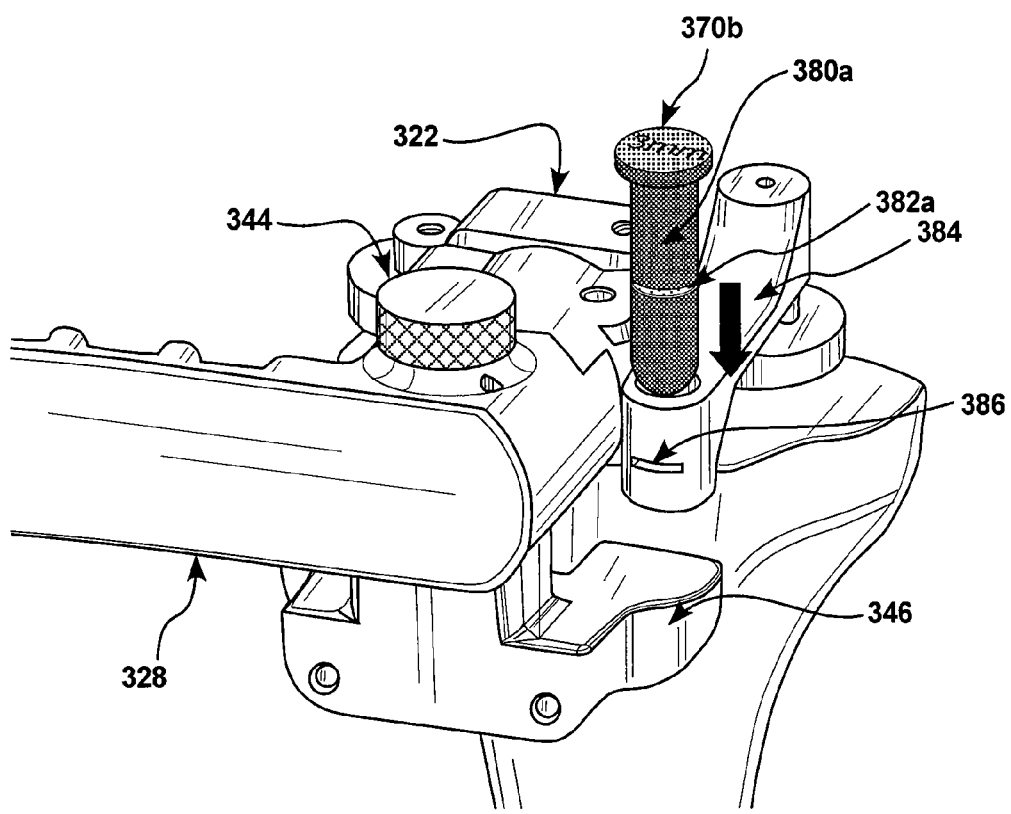
Figure 11C:
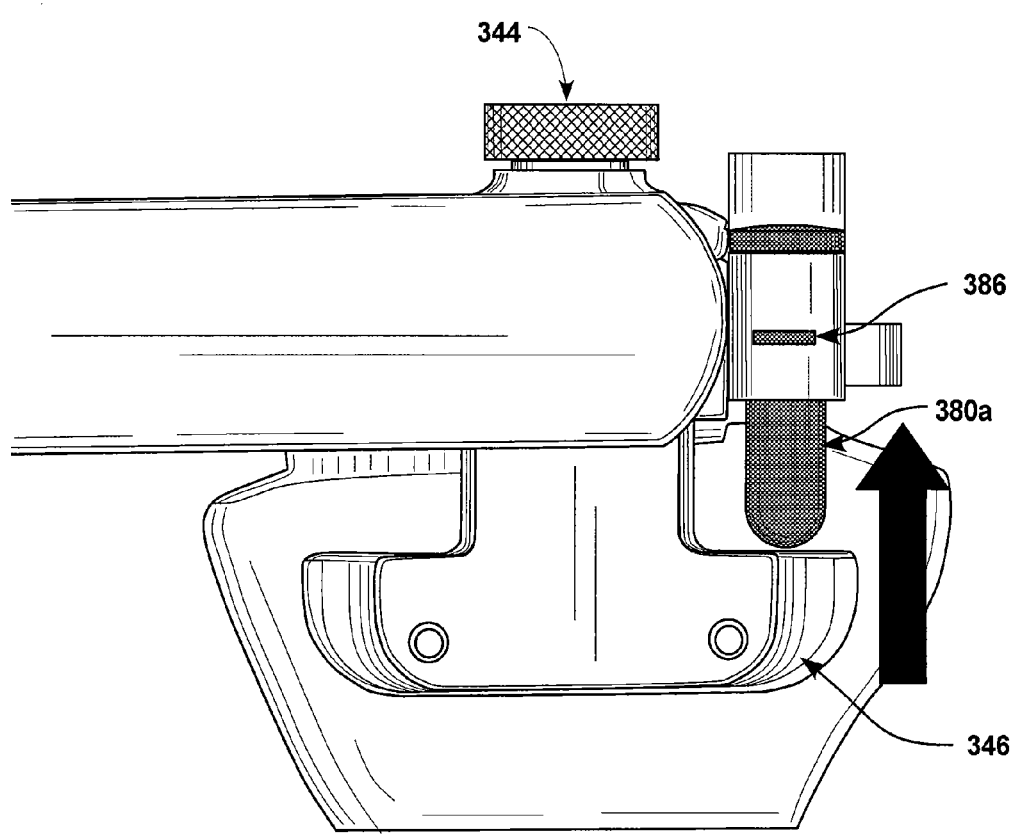
Figure 11D:
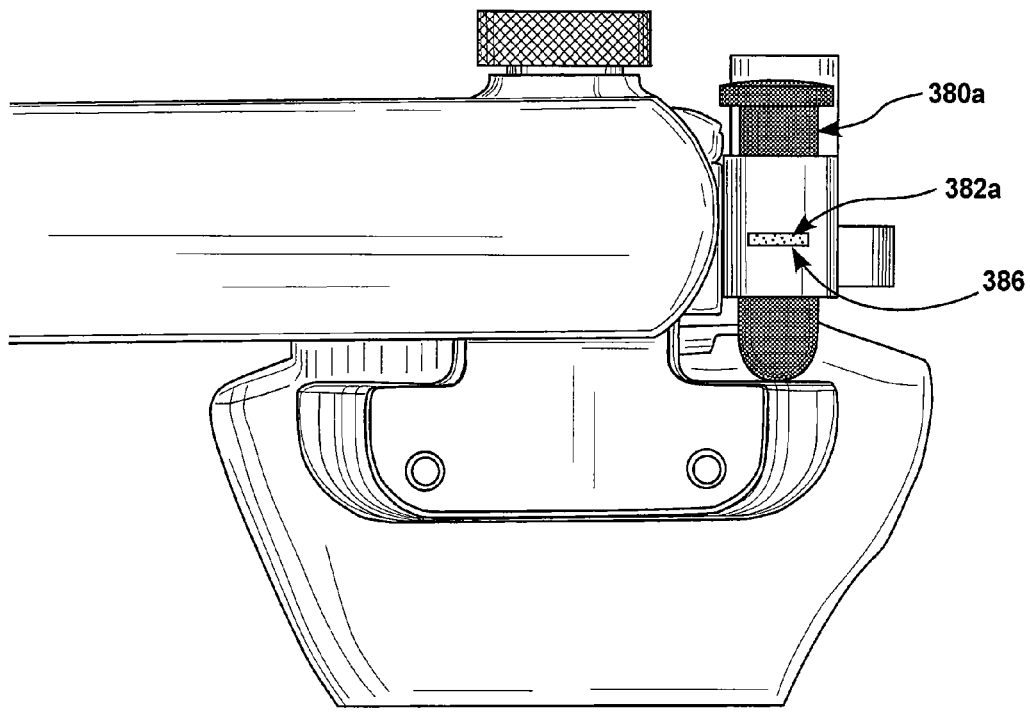
Figure 11E:
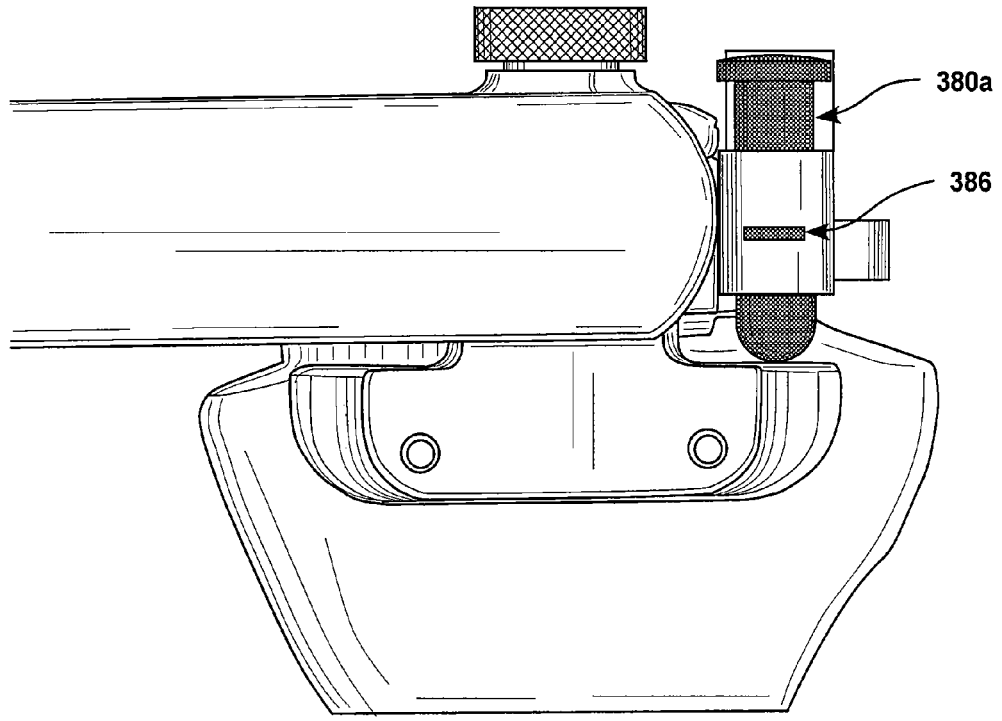

Turning now to FIG. 11B, in this embodiment, as in the previous one, gauge 380a may be inserted into a depth arm 384 having an aperture 386 (in this embodiment slot-shaped rather than round). As shown in FIGS. 11C and 11D, knob 344 may then be adjusted to bring pin template 346 into contact with one end of gauge 380a (FIG. 11C) and then to push up gauge 380a until marker 382a shows through aperture 386. If the user turns knob 344 too far, as in FIG. 11E, marker 382b is no longer visible through aperture 386, so user will know to turn knob in the opposite direction to adjust the bone cut height.

The present invention may be embodied in other specific forms without departing from the essential characteristics thereof. For example, in alternative embodiments method steps may be deleted, added or performed in a different order than that described above. In one embodiment, for example, it may be possible to perform the anterior/posterior adjustment prior to the varus/valgus adjustment. Thus, the embodiments described above as well as alternative embodiments and equivalents are intended to be included within the scope of the present invention, which is set forth in the following claims. While the description has been geared to work with a tibia, the device, method and system may be used with other bones. All elements and steps described are preferably included but may be omitted or replaced with other elements and steps.

Broadly, this writing discloses at least the following concepts.

CONCEPT 1. A method for positioning a bone cut on a tibia, the method comprising:
  coupling a bone cut positioning apparatus with a tibia;
  adjusting the positioning apparatus in a varus/valgus orientation relative to the tibia;
  adjusting the positioning apparatus in an anterior/posterior orientation relative to the tibia; and
  adjusting the positioning apparatus up or down to select a tibial bone resection level.

CONCEPT 2. A method as in concept 1, further comprising:
  before adjusting in the varus/valgus orientation, attaching a laser light emitter to an arm of the positioning apparatus, wherein attaching the emitter to the positioning apparatus activates the emitter such that it can emit laser light and wherein adjusting the apparatus in the varus/valgus orientation comprises moving emitted laser light to shine along approximately a midline of an anterior surface of the tibia; and
  before adjusting in the anterior/posterior orientation, detaching the laser light emitter from the arm and reattaching it at or near an opposite end of the arm, wherein adjusting the apparatus in the anterior/posterior orientation comprises moving emitted laser light to shine along approximately a midline of a side of the tibia.

CONCEPT 3. A method as in concept 2, wherein the side of the tibia comprises a medial side.

CONCEPT 4. A method as in concept 2, wherein coupling the bone cut positioning apparatus with the tibia comprises:
  coupling a tibial attachment member with a proximal end of the tibia; and
  coupling the arm of the positioning apparatus with the tibial attachment member, wherein the arm extends around the tibia approximately 90 degrees from a first end of the arm anterior to the tibia to a second end of the arm lateral or medial to the tibia.

CONCEPT 5. A method as in concept 4, wherein the arm attaches to the tibial attachment member via magnetic connection and the laser light emitter attaches to the arm via magnetic connection.

CONCEPT 6. A method as in concept 1, wherein the adjusting steps comprise adjusting a screw coupled with a captured ball to move a portion of the positioning apparatus about a pivot.

CONCEPT 7. A method as in concept 1, further comprising using the positioning apparatus to attach a bone cutting guide to the tibia.

CONCEPT 8. A method as in concept 7, further comprising:
  removing the positioning apparatus from the tibia and the cutting guide; and
  making at least one cut on the tibia guided by the cutting guide.

CONCEPT 9. A method for positioning a bone cut on a tibia, the method comprising:
  coupling a bone cut positioning apparatus with a tibia;
  coupling a laser light emitter with the positioning apparatus at or near one end of an arm of the apparatus, such that when the emitter is coupled with the apparatus is emits light;
  adjusting the positioning apparatus in a varus/valgus orientation to shine the emitted light approximately along a midline of an anterior surface of the tibia;
  coupling the laser light emitter with the positioning apparatus at or near an opposite end of the arm, such that when the emitter is coupled with the apparatus is emits light;
  adjusting the positioning apparatus in an anterior/posterior orientation to shine the light approximately along a midline of a side of the tibia; and
  adjusting the positioning apparatus up or down to select a tibial bone resection level.

CONCEPT 10. A method as in concept 9, further comprising attaching a tibial cutting guide to the tibia, using the adjusted positioning apparatus.

CONCEPT 11. A method as in concept 10, further comprising:

removing the positioning apparatus from the tibia and the cutting guide; and making at least one cut on the tibia guided by the cutting guide.

CONCEPT 12. A device for positioning a bone cut on a tibia, the device comprising:

a tibial attachment member;

an arm attachable to the tibial attachment member and extending in an arc of approximately 90 degrees;

a laser light emitter attachable to the arm at a first position at or near one end of the arm an a second position at or near an opposite end of the arm;

a varus/valgus adjustment member for moving the arm to direct light emitted by the emitter in the first position approximately along a midline of an anterior surface of the tibia;

an anterior/posterior adjustment member for moving the arm to direct light emitted by the emitter in the second position approximately along a midline of a side of the tibia; and a bone resection level adjustment member for selecting a level for resecting the tibia.

CONCEPT 13. A device as in concept 12, wherein the tibial attachment member comprises independently movable medial and lateral feet for contacting the medial and lateral articular surfaces of the tibia.

CONCEPT 14. A device as in concept 12, wherein the varus/valgus adjustment member comprises a first captured ball and captured screw that rotates the tibial attachment member about a first pivot point, and wherein the anterior/posterior adjustment member comprises a second capture ball and captured screw that rotates the tibial attachment member about a second pivot point.

CONCEPT 15. A device as in concept 12, wherein the laser light emitting member attaches to the arm at the first position and the second position via magnetic force.

CONCEPT 16. A device as in concept 15, wherein the arm attaches to the tibial attachment member via magnetic force.

CONCEPT 17. A device as in concept 12, further comprising a tibial cutting guide holder, wherein adjustments of the adjustment members adjust a position of the cutting guide holder.

CONCEPT 18. A device as in concept 12, further comprising a depth gauge coupled with the bone resection level adjustment member.

CONCEPT 19. A system for positioning a bone cut on a tibia, the system comprising:

a tibial cutting guide; and a tibial bone cut positioning device comprising:

a tibial attachment member;

an arm attachable to the tibial attachment member and extending in an arc of approximately 90 degrees;

a laser light emitter attachable to the arm at a first position at or near one end of the arm an a second position at or near an opposite end of the arm;

a varus/valgus adjustment member for moving the arm to direct light emitted by the emitter in the first position approximately along a midline of an anterior surface of the tibia;

an anterior/posterior adjustment member for moving the arm to direct light emitted by the emitter in the second position approximately along a midline of a side of the tibia; and a bone resection level adjustment member for selecting a level for resecting the tibia.

CONCEPT 20. A system as in concept 19, wherein the tibial cutting guide holder is moveable relative to the arm to move the tibial cutting guide into contact with the tibia.

CONCEPT 21. A system as in concept 19, further comprising at least one reference pin for removably attaching the tibial attachment member of the guide positioning device to the tibia.

CONCEPT 22. A system as in concept 19, further comprising at least one cutting guide fastener for attaching the tibial cutting guide to the tibia.

CONCEPT 23. A system as in concept 19, wherein the laser light emitting member emits light in a linear or planar configuration that may be directed along the tibia.

CONCEPT 24. A system as in concept 19, wherein the laser light emitting member attaches to the arm at the first position and the second position via magnetic force.

CONCEPT 25. A system as in concept 19, wherein the arm attaches to the tibial attachment member via magnetic force.

CONCEPT 26. A system as in concept 19, further comprising at least one depth gauge removably couplable with the bone cut positioning device.

CONCEPT 27. A system as in concept 26, wherein the depth gauge comprises a slidable member adjustable by moving the bone resection level adjustment member and including at least one indicator to indicate to a user when a desired bone cut level has been reached.

CONCEPT 28. A system as in concept 27, wherein the at least one depth gauge comprises multiple depth gauges provided as a set, each gauge having an indicator at a different depth for facilitating a different bone resection level.

CONCEPT 29. A system as in concept 28, wherein the multiple depth gauges comprise three gauges having indicators at 3 mm, 9 mm and 10 mm of depth.

CONCEPT 30. A system as in concept 27, wherein the indicator is selected from the group consisting of an LED, a colored marker, a reflective marker and a tactile element.

Broadly this writing discloses at least the following method. A method for positioning a bone cut on a bone may involve: coupling a bone cut positioning apparatus with a body bone; adjusting the positioning apparatus in a varus/valgus orientation relative to the body bone; adjusting the positioning apparatus in an anterior/posterior orientation relative to the body bone; and adjusting the positioning apparatus up or down to select a bone resection level.

The invention claimed is:

1. A method for positioning a bone cut on a tibia, the method comprising:

coupling a bone cut positioning apparatus to a tibia, the positioning apparatus including a bone cutting guide;

attaching a laser light emitter to a swing arm of the positioning apparatus, the attaching including activating the laser light emitter such that it can emit laser light;

positioning the swing arm and the laser light emitter into a first orientation relative to the tibia;

adjusting, with the swing arm and the laser light emitter in the first orientation, the positioning apparatus in a varus/valgus orientation relative to the tibia, including using emitted laser light from the laser light emitter to position the bone cutting guide in reference to an anterior surface of the tibia;

positioning, by pivoting, the swing arm and the laser light emitter into a second orientation such that the laser light emitter can emit laser light to provide orientation along a medial or a lateral surface of the tibia;

adjusting, with the laser light emitter in the second orientation, the positioning apparatus in an anterior/posterior orientation relative to the tibia, including using emitted laser light from the laser light emitter to position the bone cutting guide in reference to the medial or the lateral surface of the tibia; and adjusting the positioning apparatus up or down to select a tibial bone resection level wherein at least one of the adjusting the positioning apparatus operations includes adjusting a screw coupled with a captured ball to move a portion of the positioning apparatus about a pivot, the screw coupled with the captured ball via a threaded shaft through the captured ball.

2. A method as in claim 1, wherein adjusting the positioning apparatus in the anterior/posterior orientation includes using emitted laser light from the laser light emitter to position the bone cutting guide in reference to the medial surface of the tibia.

3. A method as in claim 1, wherein coupling the bone cut positioning apparatus to the tibia comprises:

coupling a tibial attachment member with a proximal end of the tibia; and coupling the swing arm of the positioning apparatus with the tibial attachment member, wherein the swing arm pivots around the tibia approximately 90 degrees from the first orientation, anterior to the tibia, to the second orientation, lateral or medial to the tibia.

4. A method as in claim 3, wherein the swing arm attaches to the tibial attachment member via a magnetic connection and the laser light emitter attaches to the swing arm via a magnetic connection.

5. A method as in claim 1, further comprising using the positioning apparatus to couple the bone cutting guide to the tibia.

6. A method as in claim 5, further comprising:

making at least one cut on the tibia guided by the bone cutting guide.

7. A method for positioning a bone cut on a tibia, the method comprising:

coupling a bone cut positioning apparatus with a tibia;

coupling a laser light emitter to the positioning apparatus at or near a first end of a swing arm of the apparatus, such that when the emitter is coupled with the apparatus it emits light;

adjusting the positioning apparatus in a varus/valgus orientation to shine the emitted light approximately along a midline of an anterior surface of the tibia;

pivoting the first end of the swing arm with the laser light emitter into a position adjacent to a side of the tibia;

adjusting the positioning apparatus in an anterior/posterior orientation to shine the emitted light approximately along a midline of a side of the tibia; and adjusting the positioning apparatus up or down to select a tibial bone resection level wherein at least one of the adjusting the positioning apparatus operations includes adjusting a screw coupled with a captured ball to move a portion of the positioning apparatus about a pivot, the screw coupled with the captured ball via a threaded shaft through the captured ball.

8. A method as in claim 7, further comprising attaching a tibial cutting guide to the tibia, using the adjusted positioning apparatus.

9. A method as in claim 8, further comprising:

removing the positioning apparatus from the tibia and the cutting guide; and making at least one cut on the tibia guided by the cutting guide.

10. The method of claim 7, wherein coupling the laser light emitter to the positioning apparatus includes magnetically coupling the laser light emitter to the first end of the swing arm.

11. The method of claim 10, wherein magnetically coupling the laser light emitter to the first end of the swing arm includes automatically activating the laser light emitter.

12. The method of claim 7, further including removing the laser light emitter from the first end of the swing arm.

13. The method of claim 12, wherein removing the laser light emitter from the first end of the swing arm automatically deactivates the laser light emitter.

* * * * *